United States Patent
Furusawa

(10) Patent No.: US 8,357,415 B2
(45) Date of Patent: Jan. 22, 2013

(54) METHOD FOR PRODUCING ORALLY ADMINISTRABLE EDIBLE AGENT OF AGGREGATED SUBTANCE-CONTAINING LAMINATE FILM FORM AND ORALLY ADMINISTRABLE EDIBLE AGENT OF AGGREGATED SUBSTANCE-CONTAINING LAMINATE FILM FORM

(75) Inventor: Kayo Furusawa, Izumi-gun (JP)

(73) Assignee: Kyukyu Pharmaceutical Co., Ltd., Tokyo (JP)

( * ) Notice: Subject to any disclaimer, the term of this patent is extended or adjusted under 35 U.S.C. 154(b) by 1260 days.

(21) Appl. No.: 11/578,427

(22) PCT Filed: May 25, 2005

(86) PCT No.: PCT/JP2005/009535
§ 371 (c)(1),
(2), (4) Date: Oct. 13, 2006

(87) PCT Pub. No.: WO2005/117803
PCT Pub. Date: Dec. 15, 2005

(65) Prior Publication Data
US 2007/0237871 A1    Oct. 11, 2007

(30) Foreign Application Priority Data
Jun. 2, 2004    (JP) .................. 2004-164367

(51) Int. Cl.
*A23L 1/00*    (2006.01)
*A61J 3/10*    (2006.01)
(52) U.S. Cl. ...................... 426/465; 426/138
(58) Field of Classification Search .............. 426/465, 426/138
See application file for complete search history.

(56) References Cited

U.S. PATENT DOCUMENTS

| | | | |
|---|---|---|---|
| 3,696,188 A | 10/1972 | Fernandez et al. | |
| 2004/0137040 A1* | 7/2004 | Nogami | 424/443 |
| 2004/0180080 A1* | 9/2004 | Furusawa et al. | 424/449 |
| 2006/0062830 A1* | 3/2006 | Hayashi et al. | 424/443 |

FOREIGN PATENT DOCUMENTS

| | | |
|---|---|---|
| EP | 1 247 460 A2 | 10/2002 |
| JP | 2-26493 | 2/1990 |
| JP | 2-182154 | 7/1990 |
| JP | 5-132570 | 5/1993 |
| JP | 10-503769 | 4/1998 |
| JP | 2791317 | 6/1998 |
| JP | 2001-506640 | 5/2001 |
| JP | 2001-288074 | 10/2001 |
| JP | 2002-191343 | 7/2002 |
| JP | 2002-234070 | 8/2002 |
| WO | 98/56266 | 12/1998 |
| WO | 2004/050008 | 6/2004 |
| WO | 2005/000191 | 1/2005 |

* cited by examiner

*Primary Examiner* — D. Lawrence Tarazano
*Assistant Examiner* — Jerry W Anderson
(74) *Attorney, Agent, or Firm* — Wenderoth, Lind & Ponack, L.L.P.

(57) ABSTRACT

In pressure bonding edible layers having irregular surfaces due to the presence of aggregated substance so that the irregular surfaces face each other, an edible layer substantially free of any aggregated substance is interposed therebetween. This allows an orally administrable edible agent of aggregated substance-containing laminate film form having a multilayer structure including laminated extremely thin layers to be produced. The multilayer structure by such a pressure bonding technique can satisfy quantitative accuracy required for pharmaceutical preparations, and prevents time constraint in a drying step or the like, thereby providing a producing method with high productivity.

13 Claims, 7 Drawing Sheets

Pressure bonding technique

Lamination coating technique

METHOD FOR PRODUCING ORALLY ADMINISTRABLE EDIBLE AGENT OF AGGREGATED SUBTANCE-CONTAINING LAMINATE FILM FORM AND ORALLY ADMINISTRABLE EDIBLE AGENT OF AGGREGATED SUBSTANCE-CONTAINING LAMINATE FILM FORM

TECHNICAL FIELD

The present invention relates to a novel and improved method for producing an orally administrable edible agent of laminate film form having a multilayer structure including laminated extremely thin layers of orally administrable edible substances of drugs, quasi drugs, cosmetics and food, and an orally administrable edible agent of laminate film form.

More specifically, the present invention relates to a method for producing an orally administrable edible agent of aggregated substance-containing laminate film form including laminated extremely thin layers that are made by containing a granular or powdery aggregated substance in a coating layer and are eventually provided with an irregular surface in coating of powders, granules, fine particles, particulates, etc. that are insoluble or difficultly soluble in a coating solvent together with a base ingredient in a suspended state. The orally administrable agent consists of substances accepted as food and food additives and/or drugs and pharmaceutical additives approved for oral administration, for example, oral transmucosal patches applied to upper jaw or gingival mucosa or nasal mucosa, oral disease preventive patches applied to an affected area in oral cavity for treatment and protection, oral treatment patches, bad breath preventive patches, bad breath stop patches, pharmaceutical preparations for oral administration dissolved in oral cavity and absorbed mainly in alimentary canal, quasi drugs having a deodorizing effect or a therapeutic effect, food, etc. The present invention further relates to an orally administrable edible agent of aggregated substance-containing laminate film form.

BACKGROUND ART

Various techniques for forming orally administrable edible agents such as drugs, quasi drugs, cosmetics and food into a shape of a sheet or a film have been proposed.

For example, Patent Documents 1 and 2 describe a method for producing food having a multilayer structure by feeding edible materials of different types and/or blend-ratio into hopper-chambers respectively which are partitioned off a hopper by partition plates, forming a plurality of primary rolled sheets of strip form by a primary common mill roll below the hopper-chambers, superposing the sheets one on another with a certain space therebetween in a direction perpendicular to a longitudinal direction of the sheets during conveyance, and rolling the superposed sheets by a secondary mill roll to bond them to each other. This method is, however, adapted to form a thick multilayer sheet having plasticity by rolling, and cannot produce orally administrable edible agents such as drugs, food, etc. formed by pressure bonding edible materials of several hundreds μm to several tens μm thick into a multilayer structure of several thousands μm to several tens μm thick.

The following is a patent document that relates to obtaining an edible multilayer structure of film form such as drugs, food, etc. of several thousands μm to several tens μm thick.

Patent Document 3 describes a preparation of sheet or tape form for administering buprenorphine to oral mucosa, a producing method including a first step of dissolving buprenorphine or a pharmacologically comparable substance in a suitable hydrophile solvent together with a water-soluble polymer capable of film formation, optionally in presence of further dissolved or suspended auxiliary agents; a second step of applying the solution or suspension to a tape or a process sheet or a foil with even thickness in a continuous process; a third step of removing most of the solvent to form a sheet-shaped or tape-shaped starting material; and a fourth step of separating the starting material by cutting or punching out into the dosage or multidosage units, and a producing method for combining the plurality of sheet-shaped or tape-shaped materials so as to form a multilayered material, but does not teach at all a specific method for producing a multilayer structure.

Patent Document 4 describes an orally administrable agent of film form having a multilayer structure including a drug-containing layer containing a water-soluble polymer as a main base ingredient, a non-adhesive layer (a difficultly water-soluble layer) that is difficultly water-soluble and placed on one surface of the drug-containing layer, and a powdery adhesive substance placed on the other surface of the drug-containing layer. As the powdery adhesive substance, carboxy vinyl polymer, polyacrylate such as sodium polyacrylate or a pharmaceutically accepted nontoxic salt thereof, acrylic acid copolymer or a pharmaceutically accepted nontoxic salt thereof, a hydrophilic cellulose derivative such as carboxymethyl cellulose and sodium salt thereof, pullulan, povidone, karaya gum, pectin, xanthan gum, tragacanth, alginic acid, gum arabic, acidic polysaccharide or a derivative thereof or a nontoxic salt thereof can be used.

A producing method disclosed in an embodiment of the Patent Document 4 includes repeatedly spreading or spraying an edible layer solution and drying the spread or sprayed edible layer solution on a petri dish made of polytetrafluoroethylene to obtain an orally administrable agent of film form having a desired multilayer structure. Such a producing method cannot be industrially used, though used in a laboratory. Further, if an edible layer solution containing a different drug, an edible layer solution maintaining an adhesive polymer in a powdery state, or powder itself is manually spread or sprayed on the formed edible layer so as to form the multilayer structure, it is difficult to spread or spray an accurate amount of orally administrable agent solution or powder to prevent control of an accurate amount of drug ingredient, and the obtained multilayer orally administrable agent of film form cannot satisfy quantitative accuracy required for pharmaceutical preparations.

Patent Document 5 filed by the applicant of this application proposes an orally administrable troche agent of film form including three layers of a covering layer (a), a drug layer I (b), and a drug layer II (c) laminated in order of a-b-c-b-a. This document discloses a method for producing the orally administrable troche agent of film form including repeatedly coating and drying each edible layer solution (a coating liquid) on a polyester delamination film to form a desired multilayer laminated structure.

In producing the orally administrable troche agent of film form having the multilayer laminated structure described in the Patent Document 5 filed by the applicant of this application, the applicant uses a coating apparatus 50 for continuously coating and drying the coating liquid on a continuously moving resin film as shown in FIG. 9. The coating apparatus 50 guides a resin film 52 set to a resin film unwinding shaft 51 into a drying oven 55 through a nip between a guide roll 53 and a doctor roll 54, and winds up the resin film 52 on a resin film winding shaft 56, thereby continuously moving the resin film 52. In the meantime, a coating liquid 58 contained in a dam portion 57 for supplying the coating liquid is coated on the resin film, and at this time, a clearance between the resin film 52 on the guide roll 53 and the doctor roll 54 is adjusted to a predetermined dimension to obtain a predetermined coating amount (see the partial enlarged view). A coating layer 58a on the resin film 52 thus formed passes through the drying oven 55 and is dried by hot air uniformly blown from a hot air blowing device 59, and a resin film 60 provided with an edible layer is wound up on the winding shaft 56 into a roll.

Then, the edible layer-formed resin film 60 wound up on the winding shaft 56 into the roll is mounted to the unwinding shaft 51 again, the coating liquid 58 of the same or different composition is supplied to the dam portion 57 for coating and drying again, and the resin film is wound up on the winding shaft 56, thereby producing a resin film including laminated two edible layers. Repeating such coating and drying steps allows the orally administrable troche agent of film form having a desired multilayer structure to be produced with higher productivity than the conventional methods described above.

However, it has been found that even with the coating method as shown in FIG. 9, accurate control of a coating amount of the coating liquid 58 is difficult in producing the orally administrable edible agent of film form having the multilayer structure by repeating the coating and drying steps, and quantitative accuracy required for pharmaceutical preparations cannot be satisfied, like the conventional methods described above.

Specifically, in a first coating step, the clearance between the doctor roll 54 and the resin film 52 can be set to the predetermined dimension to accurately control the coating amount at a predetermined value. However, a thickness of a dried edible layer formed in a drying step after the first coating step varies depending on minor variation of condition of the drying step and environmental conditions such as daily temperature and humidity. Therefore, in a second coating step, even if the clearance dimension between the doctor roll 54 and the resin film 52 is accurately set, a coating thickness of the second edible layer further varies depending on variation of the coating thickness of the first edible layer, since a coating thickness of the coating liquid 58 is determined by a clearance between an upper surface of the first dried edible layer and the doctor roll 54. It is significantly difficult to measure the variation of the thickness of the first edible layer 58a after the drying step.

Such an inaccurate coating amount of the coating liquid tends to increase as the number of coating and drying steps increases. Further, as the number of coating and drying steps increases, drying time increases. More specifically, drying time for the second edible layer is 1.5 times longer than that for the first layer, and drying time for a third layer is twice longer than that for the first layer.

Patent Document 1: WO98/56266
Patent Document 2: Japanese Patent Laid-Open No. 2002-191343
Patent Document 3: National Publication of International Patent Application No. 2001-506640
Patent Document 4: Japanese Patent No. 2791317
Patent Document 5: Japanese Patent Laid-Open No. 2001-288074

DISCLOSURE OF THE INVENTION

In such a situation, in order to obtain an orally administrable edible agent having a multilayer structure, the inventor attempts to coat and dry an edible layer solution (a coating liquid) on a resin film to form an edible layer having a predetermined thickness, pressurize resin films, with the edible layers thereon facing each other, at back surfaces to pressure bond the edible layers, and delaminate one of the resin films sandwiching the bonded edible layers.

Specifically, if the edible layer contains at least one edible substance having a thermoplastic property, and is heated to a temperature slightly higher than a glass transition point of the thermoplastic edible substance, the edible layer reaches a rubber elastic range. It has been found that if the resin films are pressurized, with the edible layers thereof facing each other, at back surfaces in this state, the edible layers are reliably bonded together, and an orally administrable edible agent having a multilayer structure can be obtained.

Such a pressure bonding technique is used in producing an orally administrable edible agent of film form having a multilayer structure to provide an orally administrable edible agent of laminate film form having a multilayer structure including laminated extremely thin layers with high productivity that can satisfy quantitative accuracy required for pharmaceutical preparations, and prevents time constraint in a drying step or the like.

Particularly, a laminated structure obtained by a method for producing an orally administrable edible agent of laminate film form using the pressure bonding technique is characterized in that each of laminated edible layers is definitely divided. Specifically, in the laminated structure obtained by the pressure bonding technique, as shown in a sectional photomicrograph in FIG. 8 observed using "Digital microscope BS-D8000II" (trade name, produced by Sonic Co., LTD)", a boundary X between the edible layers appears clear and each of the laminated edible layers can be definitely identified. On the other hand, in a laminated structure obtained by a conventional lamination coating technique of repeating coating and drying steps for lamination, a boundary Y between edible layers appears unclear and blurred, and each of the laminated edible layers cannot be definitely identified. Specifically, it can be seen that in the lamination coating technique, ingredients of the edible layers permeate and mix in the boundary between the edible layers, while in the pressure bonding technique, ingredients of the edible layers do not permeate and mix. The pressure bonding technique has advantages of improving quantitative accuracy and preventing time constraint in a drying step or the like, and preventing drug decomposition or unintended reactions caused by mixing of part of the ingredients of the edible layers to improve preservation stability.

However, it has been found that when edible layers containing an aggregated substance such as powders, granules, fine particles, or particulates that are insoluble or difficultly soluble in a coating solvent and thus having irregular surfaces are pressure bonded so that the irregular surfaces facing each other, the edible layers are not bonded together and are easily delaminated. The delamination tends to occur when a height difference of the irregularities is 20 μm or more, and more remarkably occur when the difference is 30 μm or more. The aggregated substance that forms the irregular surface in the edible layer is mainly an active ingredient having a physiological activity, and this problem cannot be overlooked in pharmaceuticals or functional food.

An object of the present invention is to provide a novel and improved method for producing an orally administrable edible agent of aggregated substance-containing laminate film form having a multilayer structure including laminated extremely thin layers with high productivity that allows extremely thin edible layers containing a granular or powdery aggregated substance and eventually having irregular surfaces to be reliably pressure bonded, can satisfy quantitative accuracy required for pharmaceutical preparations, and prevents time constraint in a drying step or the like, and further to provide an orally administrable edible agent of aggregated substance-containing laminate film form having a multilayer structure obtained by the method.

Specifically, a method for producing an orally administrable edible agent of aggregated substance-containing laminate film form according to claim 1 of the present invention is characterized in that, when edible layers each having irregular surface due to the presence of aggregated substance are pressure bonded with the irregular surfaces thereof facing each other, an edible layer substantially free of any aggregated substance is interposed between the edible layers.

An orally administrable edible agent of aggregated substance-containing laminate film form of the present invention is characterized in that an edible layer substantially free of any aggregated substance is interposed between two edible layers containing an aggregated substance.

According to the producing method, the edible layer substantially free of any aggregated substance is interposed to reliably pressure bond the edible layers having the irregular surfaces due to the presence of aggregated substance without forming a desired number of edible layers by repeating coating and drying of a coating liquid on a resin film. A plurality of extremely thin edible layers are laminated using the pressure bonding technique, thereby allowing an orally administrable edible agent of aggregated substance-containing laminate film form to be produced with high productivity and allowing quantitative accuracy required for pharmaceutical preparations to be satisfied.

According to the orally administrable edible agent, the edible layer substantially free of any aggregated substance is interposed to reliably pressure bond and laminate the edible layers having the irregular surfaces due to the presence of aggregated substance to provide an orally administrable edible agent of aggregated substance-containing laminate film form. The plurality of extremely thin edible layers can be pressure bonded and laminated, thereby allowing quantitative accuracy required for pharmaceutical preparations to be satisfied, and preventing drug decomposition or unintended reactions caused by mixing of part of ingredients of the edible layers to improve preservation stability.

The "edible layer substantially free of any aggregated substance" means that the surface of the edible layer is visually substantially smooth, and includes an edible layer having a substantially smooth surface in single layer formed by coating even if the edible layer contains a trace quantity of aggregated substance such as powders, granules, fine particles, or particulates that are insoluble or difficultly soluble in a coating solvent, and so the edible layer may contain an aggregated substance in an amount that does not substantially form an irregular surface in the layer. Even if the edible layer contains particles (aggregated substance) such as titanium oxide that are insoluble in a solvent and the particle size thereof is extremely small, an irregular surface is not formed in the layer, and thus the edible layer may contain an aggregated substance having a minute particle size. However, even if the particle size is extremely minute, a substance that is coagulated in a coating liquid may form an irregular surface in the edible layer. In any case, for the edible layer substantially free of any aggregated substance in the present invention, a height difference of irregularities is preferably 10 µm or less, more preferably 5 µm or less in single layer formed by coating.

A method for producing an orally administrable edible agent of aggregated substance-containing laminate film form according to claim 2 of the present invention is characterized by including:

(A) an irregular surface edible layer forming step for forming an irregular surface edible layer having an irregular surface with a predetermined thickness by directly or indirectly coating a coating liquid containing an aggregated substance on a resin film;

(B) a smooth surface edible layer forming step for forming an edible layer having a substantially smooth surface with a predetermined thickness on a resin film by coating;

(C) a pressure bonding step for joining together the edible layers formed on the resin films obtained in the irregular surface edible layer forming step (A) and the smooth surface edible layer forming step (B) so that the edible layers face each other, and pressurizing the resin films at back surfaces to bond the edible layers together;

(D) a resin film delaminating step for delaminating only the resin film used in the smooth surface edible layer forming step (B) among the resin films on both sides of the bonded edible layers obtained in the pressure bonding step (C);

(E) a multiple edible layer pressure bonding step for joining together the bonded edible layers having a substantially smooth surface formed on the resin film obtained in the resin film delaminating step (D) and an irregular surface edible layer made of the same or different ingredient as or from the foregoing irregular surface edible layer and provided with an irregular surface due to the presence of aggregated substance formed on the resin film in the irregular surface edible layer forming step (A) so that the edible layers face each other, and pressurizing the resin films at back surfaces to bond the edible layers together; and (F) a resin film separating step for delaminating at least one of the resin films on both sides of the bonded edible layers obtained in the multiple edible layer pressure bonding step (E).

A method for producing an orally administrable edible agent of aggregated substance-containing laminate film form according to claim 3 of the present invention is characterized by including:

(A) an irregular surface edible layer forming step for forming an irregular surface edible layer having an irregular surface with a predetermined thickness by directly or indirectly coating a coating liquid containing an aggregated substance on a resin film;

(B) a smooth surface edible layer forming step for forming an edible layer having a substantially smooth surface with a predetermined thickness on a resin film by coating;

(C) a pressure bonding step for joining together the edible layers formed on the resin films obtained in the irregular surface edible layer forming step (A) and the smooth surface edible layer forming step (B) so that the edible layers face each other, and pressurizing the resin films at back surfaces to bond the edible layers together;

(D) a resin film delaminating step for delaminating only the resin film used in the smooth surface edible layer forming step (B) among the resin films on both sides of the bonded edible layers obtained in the pressure bonding step (C);

(G) a multiple bonded edible layers pressure bonding step for joining together the bonded edible layers having a substantially smooth surface formed on the resin film obtained in the resin film delaminating step (D) and bonded edible layers made of the same or different ingredient as or from the foregoing bonded edible layers and provided with a substantially smooth surface formed on the resin film through the irregular surface edible layer forming step (A), the smooth surface edible layer forming step (B), the pressure bonding step (C), and the resin film delaminating step (D) so that the edible layers face each other, and pressurizing the resin films at back surfaces to bond the edible layers together; and (H) a resin film separating and removing step for delaminating at least one of the resin films on both sides of the bonded edible layers obtained in the multiple bonded edible layers pressure bonding step (G).

A method for producing an orally administrable edible agent of aggregated substance-containing laminate film form according to claim 4 of the present invention is characterized by including:

(A) an irregular surface edible layer forming step for forming an irregular surface edible layer having an irregular surface with a predetermined thickness by directly or indirectly coating a coating liquid containing an aggregated substance on a resin film;

(I) a coating smooth surface edible layer forming step for forming an edible layer having a substantially smooth surface with a predetermined thickness by coating on the irregular surface of the edible layer formed on the resin film obtained in the irregular surface edible layer forming step (A);

(J) a coating edible layer pressure bonding step for joining together a coating laminated edible layer having a substantially smooth surface formed on the resin film obtained in the coating smooth surface edible layer forming step (I), and an irregular surface edible layer made of the same or different ingredient as or from the foregoing irregular surface edible layer and provided with an irregular surface due to the presence of aggregated substance formed on the resin film in the irregular surface edible layer forming step (A) so that the edible layers face each other, and pressurizing the resin films at back surfaces to bond the edible layers together; and (K) a resin film delaminating step for delaminating at least one of the resin films on both sides of the bonded edible layers obtained in the coating edible layer pressure bonding step (J).

A method for producing an orally administrable edible agent of aggregated substance-containing laminate film form according to claim 5 of the present invention is characterized by including:

(A) an irregular surface edible layer forming step for forming an irregular surface edible layer having an irregular surface with a predetermined thickness by directly or indirectly coating a coating liquid containing an aggregated substance on a resin film;

(I) a coating smooth surface edible layer forming step for forming an edible layer having a substantially smooth surface with a predetermined thickness by coating on the irregular surface of the edible layer formed on the resin film obtained in the irregular surface edible layer forming step (A);

(L) a multiple coating laminated edible layer pressure bonding step for joining together a coating laminated edible layer having a substantially smooth surface formed on the resin film obtained in the coating smooth surface edible layer forming step (I), and a coating laminated edible layer made of the same or different ingredient as or from the foregoing coating laminated edible layer and provided with a substantially smooth surface formed on the resin film through the irregular surface edible layer forming step (A) and the coating smooth surface edible layer forming step (I) so that the edible layers face each other, and pressurizing the resin films at back surfaces to bond the edible layers together; and (M) a resin film delaminating and removing step for delaminating at least one of the resin films on both sides of the bonded edible layers joined in the multiple coating laminated edible layer pressure bonding step (L).

A method for producing an orally administrable edible agent of aggregated substance-containing laminate film form according to claim 6 of the present invention is characterized by including:

(A) an irregular surface edible layer forming step for forming an irregular surface edible layer having an irregular surface with a predetermined thickness by directly or indirectly coating a coating liquid containing an aggregated substance on a resin film;

(B) a smooth surface edible layer forming step for forming an edible layer having a substantially smooth surface with a predetermined thickness on a resin film by coating;

(C) a pressure bonding step for joining together the edible layers formed on the resin films obtained in the irregular surface edible layer forming step (A) and the smooth surface edible layer forming step (B) so that the edible layers face each other, and pressurizing the resin films at back surfaces to bond the edible layers together;

(D) a resin film delaminating step for delaminating only the resin film used in the smooth surface edible layer forming step (B) among the resin films on both sides of the bonded edible layers obtained in the pressure bonding step (C);

(N) a multiple coating bonded edible layers pressure bonding step for joining together bonded edible layers having a substantially smooth surface formed on the resin film obtained in the resin film delaminating step (D) and a coating laminated edible layer made of the same or different ingredient as or from the foregoing bonded edible layer and provided with an edible layer having a substantially smooth surface with a predetermined thickness formed by coating on the irregular surface of the edible layer formed on the resin film in the irregular surface edible layer forming step (A) so that the edible layers face each other, and pressurizing the resin films at back surfaces to bond the edible layers together; and (O) a resin film removing step for delaminating at least one of the resin films on both sides of the bonded edible layers joined in the multiple coating bonded edible layers pressure bonding step (N).

According to the producing method in claims 2 to 6 of the present invention, the edible layers containing the aggregated substance and having irregular surfaces are pressure bonded in a state that the edible layer having the substantially smooth surface with the predetermined thickness are interposed therebetween, thereby allowing an orally administrable edible agent of aggregated substance-containing laminate film form having a multilayer structure that has been produced only by a lamination coating technique to be efficiently produced. The "edible layer having a substantially smooth surface" in the producing method according to claims 2 to 6 means an edible layer that is substantially free of granular or powdery aggregated substance that is insoluble or difficultly soluble in a coating solvent, and eventually has a substantially smooth surface.

In the irregular surface edible layer forming step (A), the irregular surface edible layer may be coated on the resin film (direct coating), or as required, a covering layer, a support layer or an adhesive layer may be first coated on the resin film, and then the irregular surface edible layer may be coated thereon (indirect coating).

Ingredients of the edible layers having the substantially smooth surfaces formed in the smooth surface edible layer forming step (B) and the coating smooth surface edible layer forming step (I) are not limited as long as they contain an edible thermoplastic substance, but preferably substantially the same as ingredients except the aggregated substance of the edible layer having the irregular surface formed in the irregular surface edible layer forming step (A). The ratio of composition is preferably substantially the same as the percentage of the ingredients except the aggregated substance. The thickness of the edible layers having the substantially smooth surfaces formed in the smooth surface edible layer forming step (B) and the coating smooth surface edible layer forming step (I) is preferably 10 μm or more, more preferably 10 to 50 μm.

The term "coating laminated edible layer" in claims 4 to claim 6 is used as the term that means a laminated edible layer having a substantially smooth surface in which a smooth surface edible layer is coated and laminated on the irregular surface edible layer formed on the resin film.

Further, for a preferred embodiment of the present invention described above, the method for producing an orally administrable edible agent of aggregated substance-containing laminate film form according to claim 7 of the present invention is characterized in that, in any one of claims 1 to 6, a pressure when the edible layers are joined and pressure bonded is 0.05 to 1.5 MPa, and a temperature of the edible layers at that time is 30° C. to 70° C.

The method for producing an orally administrable edible agent of aggregated substance-containing laminate film form according to claim 8 of the present invention is characterized in that, in claim 7, after the edible layers are pressure bonded and before the resin film is delaminated from the bonded edible layers, the bonded edible layers are cooled to a temperature 10° C. or more lower than the temperature of the edible layers in the pressure bonding, and the temperature of the cooled edible layers is kept higher than 0° C.

The method for producing an orally administrable edible agent of aggregated substance-containing laminate film form according to claim 9 of the present invention is characterized in that, in any one of claims 1 to 6, a thickness of the edible layer containing an aggregated substance and having an irregular surface is 25 to 300 μm.

The method for producing an orally administrable edible agent of aggregated substance-containing laminate film form according to claim 10 of the present invention is characterized in that, in any one of claims 1 to 6, the aggregated substance is an active ingredient having a physiological activity.

The method for producing an orally administrable edible agent of aggregated substance-containing laminate film form according to claim 11 of the present invention is characterized in that, in any one of claims 1 to 6, each of the edible layers to be bonded together contains an edible thermoplastic substance.

The method for producing an orally administrable edible agent of aggregated substance-containing laminate film form according to claim 12 of the present invention is characterized in that, in claim 11, the edible thermoplastic substance includes at least one selected from the group consisting of amylose, carboxymethyl cellulose potassium, carboxymethyl cellulose sodium, carboxymethyl cellulose calcium, alkyl ester alginate, sodium alginate, ethyl cellulose, eudragit, carboxymethylethylcellulose, carboxymethyl starch, carboxymethyl cellulose, agar, gelatin, shellac, dextran, dextrin, starch, tragacanth, hydroxyethylcellulose, hydroxypropylcellulose, hydroxypropylmethylcellulose, hydroxypropylmethylcellulose phthalate, polyvinylpyrrolidone, methacrylic acid copolymer, and methylcellulose phthalate.

The method for producing an orally administrable edible agent of aggregated substance-containing laminate film form according to claim 13 of the present invention is characterized in that, in any one of claims 1 to 6, each of the edible layers to be bonded together contains an edible non-thermoplastic substance and an edible thermoplasticity adding substance.

The orally administrable edible agent of aggregated substance-containing laminate film form of the present invention is characterized in that, the aggregated substance is an active ingredient having a physiological activity.

The orally administrable edible agent of aggregated substance-containing laminate film form of the present invention is characterized in that, at least one of the edible layers containing the aggregated substance and the edible layer substantially free of any aggregated substance contain an edible thermoplastic substance.

The orally administrable edible agent of aggregated substance-containing laminate film form of the present invention is characterized in that, the edible thermoplastic substance includes at least one selected from the group consisting of amylose, carboxymethyl cellulose potassium, carboxymethyl cellulose sodium, carboxymethyl cellulose calcium, alkyl ester alginate, sodium alginate, ethyl cellulose, eudragit, carboxymethylethylcellulose, carboxymethyl starch, carboxymethyl cellulose, agar, gelatin, shellac, dextran, dextrin, starch, tragacanth, hydroxyethylcellulose, hydroxypropylcellulose, hydroxypropylmethylcellulose, hydroxypropylmethylcellulose phthalate, polyvinylpyrrolidone, methacrylic acid copolymer, and methylcellulose phthalate.

The orally administrable edible agent of aggregated substance-containing laminate film form of the present invention is characterized in that, at least one of the edible layers containing the aggregated substance and the edible layer substantially free of any aggregated substance contain an edible non-thermoplastic substance and an edible thermoplasticity adding substance.

BEST MODE FOR CARRYING OUT THE INVENTION

First, a coating apparatus and a pressure bonding apparatus will be described that can be preferably used in a method for producing an orally administrable edible agent of aggregated substance-containing laminate film form according to the present invention.

Figure 9:
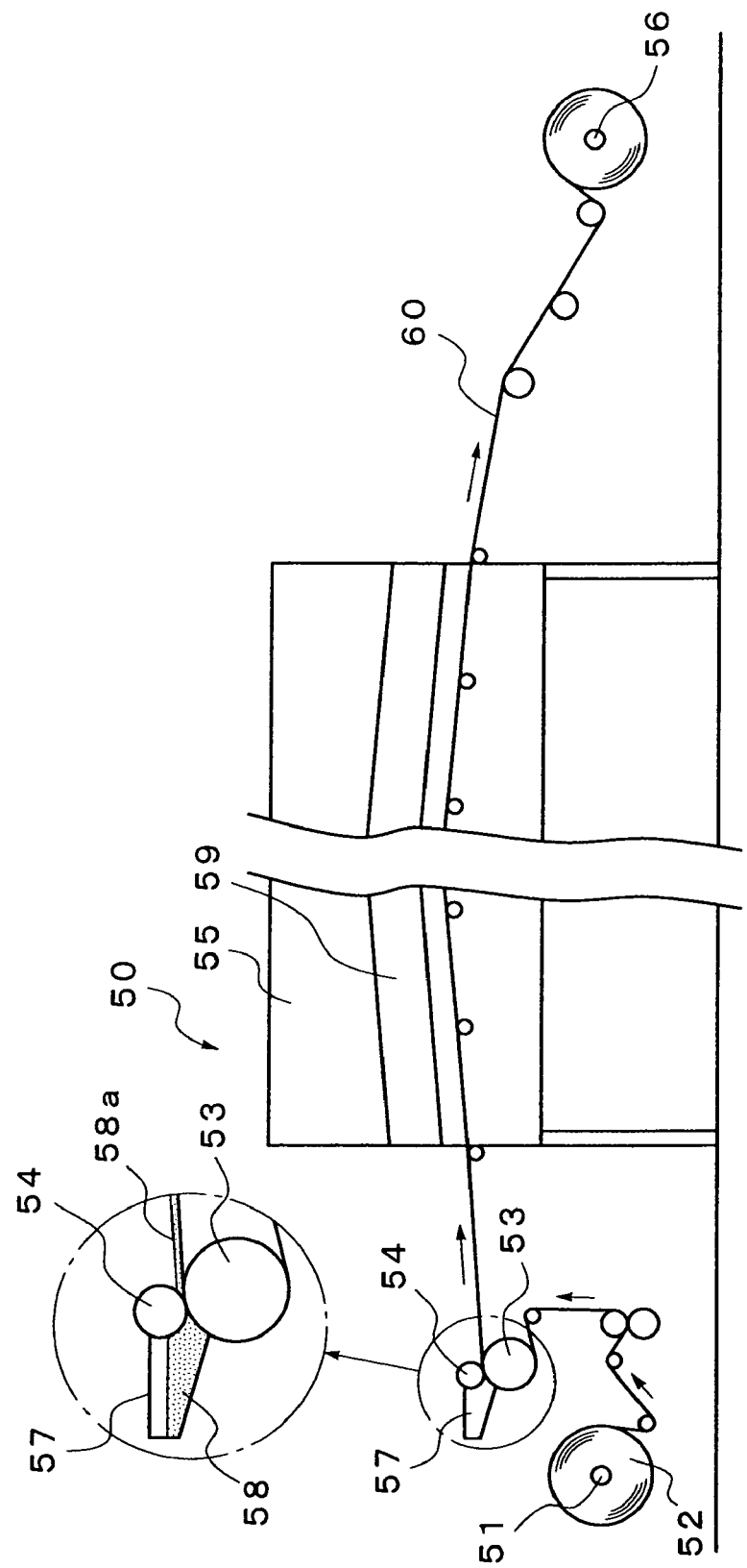
FIG. 9 illustrates an example of a coating apparatus for coating and drying an edible layer.

As a coating apparatus for coating and drying an edible layer on a surface of a resin film, a coating apparatus 50 shown in FIG. 9 may be preferably used. In the coating apparatus 50, a resin film 52 unwound from a resin film unwinding shaft 51 is wound up on a resin film winding shaft 56 through a drying oven 55 and continuously moved. In the meantime, a coating liquid 58 stored in a dam portion 57 for supplying the coating liquid is coated on the resin film 52 and dried to form an edible layer on the surface of the resin film. A coating amount of the edible layer may be controlled by adjusting a clearance between a doctor roll 54 and the resin film 52 in the dam portion 57.

Repeating coating and drying of the coating liquid several times using such a coating apparatus 50 allows a plurality of edible layers to be formed on the surface of the resin film. Also, repeating coating and drying of the coating liquid of the same or different ingredient several times allows a thickness of the edible layer of the same ingredient to be increased or allows a plurality of edible layers of various ingredients to be formed.

However, as described above, since a coating amount of the coating liquid becomes inaccurate and drying time increases as the number of coating and drying steps increases, the coating and drying steps are preferably repeated twice or three times at most, and more preferably once.

The coating apparatus 50 in FIG. 9 is used to perform a single coating step or a plurality of coating steps with the same ingredient or different ingredients to produce an edible layer-formed resin film 60 provided with a desired edible layer. Edible layer-formed resin films 60 of various types thus produced each are wound up on the winding roll 56 into a roll to form a rolled film, and then a pressure bonding apparatus 10 in FIG. 1 is used to pressure bond two edible layer-formed resin films and produce an orally administrable edible agent of laminate film form.

Figure 1:
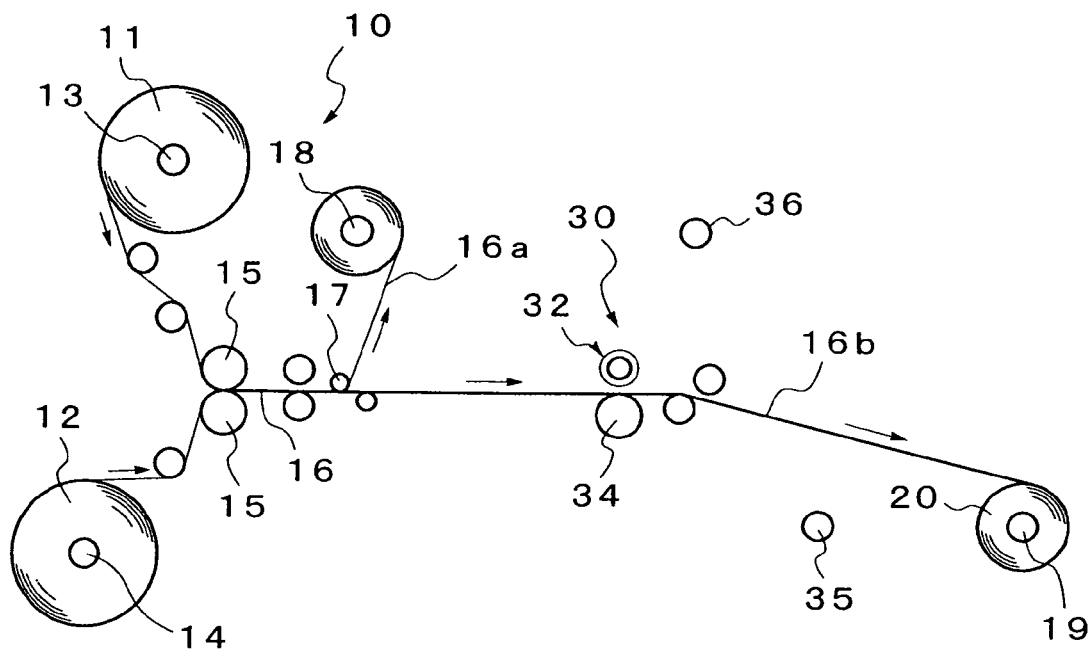
FIG. 1 illustrates an embodiment of a pressure bonding apparatus for implementing a method according to the present invention.

Specifically, the pressure bonding apparatus 10 in FIG. 1 includes: a pair of press rolls 15, 15 that draw and join the two resin films produced, for example, using the coating apparatus 50 in FIG. 9 and provided with the edible layers with a predetermined thickness on surfaces thereof so that the edible layers face each other, and pressurize the resin films at back surfaces; a delamination roll 17 that delaminates one 16a of the two resin films (an intermediate pressure bonded product) 16 sandwiching plural edible layers delivered from the press rolls and bonded together; a winding shaft 18 that winds up the delaminated film; and a winding roll 19 that winds up a plural edible layers-retained resin film (a pressure bonded product) 16b left after the delamination.

The winding roll 19 is used as a drive roll, one of the press rolls 15, 15 is used as a drive roll, and another drive roll 34 is disposed between the delamination roll 17 and the winding roll 19. These three drive rolls constitute a conveyance mechanism of the plural edible layers-retained resin film, and can convey the plural edible layers-retained resin film 16b delivered from the press rolls 15, 15 to the winding roll 19.

Figure 2:
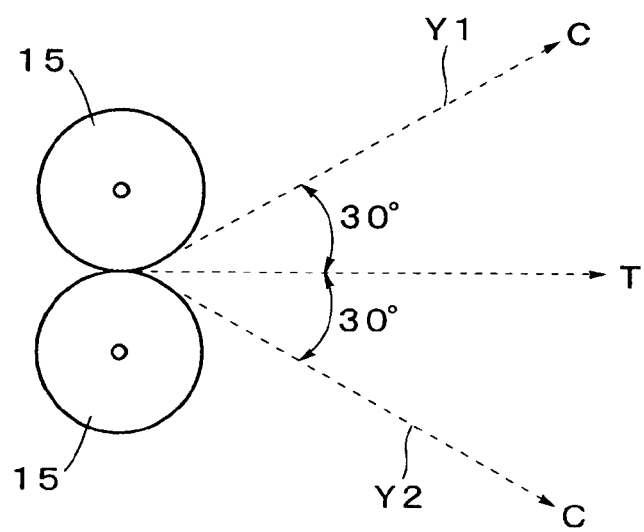
FIG. 2 illustrates a conveying direction of an intermediate pressure bonded product delivered from press rolls of the pressure bonding apparatus in FIG. 1.

A conveying direction of the plural edible layers-retained resin film 16b by the conveyance mechanism conforms to a tangential direction at a pressurization zone of the pair of press rolls 15, 15 as shown in FIG. 1, but the conveying direction may nearly or substantially, even not accurately, conform to the tangential direction so that, as shown in FIG. 2, displacement between the tangential direction T and the conveying direction C is 30° or less, preferably 15° or less, and more preferably 10° or less. In other words, the conveying direction may be within a range between the arrow Y1 and the arrow Y2 in FIG. 2.

The plural edible layers have strength sufficient to form a self-supporting film to cause the edible layers to adhere to one resin film 16a to be delaminated, thereby sometimes preventing the edible layers from being retained on the other resin film 16b. Thus, the delamination roll 17 is disposed in a position along the conveying direction of the plural edible layers-retained resin film delivered from the press rolls 15, 15, and winds up one 16a of the two resin films 16 sandwiching the bonded plural edible layers on the winding shaft 18 that draws one 16a of the two resin films 16 in a direction different from the conveying direction of the plural edible layers-retained resin film 16b. The delamination roll 17 is rotatably disposed so as to rotate with movement of one resin film 16a to be delaminated.

Figure 3:
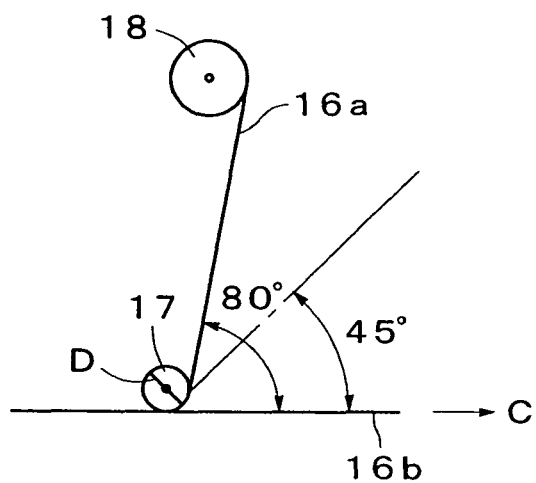
FIG. 3 illustrates a positional relationship between a delamination roll and a winding shaft for a film to be delaminated in the pressure bonding apparatus in FIG. 1.

Further, as shown in FIG. 3, the delamination roll 17 has a diameter D of 6 cm or less, preferably 5 cm or less, and one resin film is delaminated with a sharp angle along a peripheral surface of the delamination roll 17 having the small diameter to allow the plural edible layers to be reliably retained on the other intended resin film 16b. The winding shaft 18 that winds up the resin film 16a to be delaminated is disposed in a position where the resin film 16a to be delaminated is drawn at an angle of 45° or more, preferably 60° or more to the conveying direction C of the plural edible layers-retained resin film 16b with the delamination roll 17 as a starting point. In an example in FIG. 3, the winding shaft 18 is disposed in a position where the delaminated resin film 16a is drawn at an angle of about 80° to the conveying direction C.

An operation of the pressure bonding apparatus 10 according to the invention shown in FIG. 1 is as described below. One rolled film 11 provided with an edible layer on the surface is set to an upper unwinding shaft 13 of the pressure bonding apparatus 10, and another rolled film 12 provided with an edible layer is set to a lower unwinding shaft 14. These rolled films 11 and 12 are unwound at predetermined speeds, joined together so that the surfaces of the edible layers face each other, and passed through a nip between the pair of press rolls 15, 15 to pressurize the resin films at back surfaces to bond the edible layers together.

In pressurizing by the press rolls 15, 15, the press rolls 15, 15 or guide rolls in previous steps to the press rolls 15, 15 are heated by a built-in electric heater or a built-in steam heater in the rolls, and the temperature condition and the pressurization condition thereof will be described later.

The intermediate pressure bonded product 16 having passed through the press rolls 15, 15 has a structure in which both surfaces are covered with the resin films and the plural edible layers are bonded and laminated between the resin films. At the time when the intermediate pressure bonded product 16 passes through the delamination roll 17, the resin film 16a covering an upper surface is continuously delaminated, and the tip of the delaminated resin film is wound up on the delaminated film winding shaft 18.

The pressure bonded product 16b thus obtained, that is, the resin film retaining the plural edible layers is wound up on the winding roll 19 into a roll to form a plural edible layers-retained rolled film 20.

Figure 4:
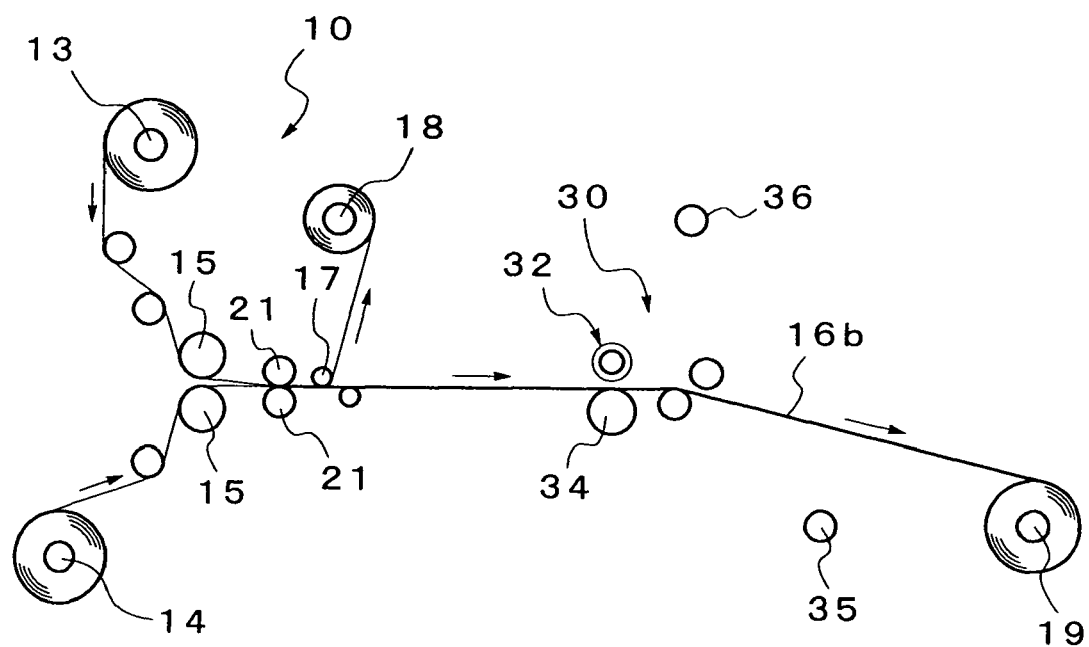
FIG. 4 illustrates an example of an operation of the pressure bonding apparatus in FIG. 1.

When the two resin films retaining the edible layers are passed through the nip between the press rolls 15, 15 and pressure bonded, air trapped between the two resin films causes poor adhesion. In this case, as shown in FIG. 4, a pair of rolls 21, 21 disposed downstream of the press rolls 15, 15 are closed by narrowing a gap therebetween, and the press rolls 15, 15 are opened by widening a gap therebetween without stopping the operation of the pressure bonding apparatus 10. This operation causes the air trapped between the two resin films to be easily forced out by the closed rolls 21, 21 and removed. After the air is removed, the press rolls 15, 15 are closed and the rolls 21, 21 are opened to return to a normal pressure bonding operation.

The method for producing an orally administrable edible agent of aggregated substance-containing laminate film form according to the present invention will be described using the coating apparatus 50 (FIG. 9) and the pressure bonding apparatus 10 (FIG. 1).

The method for producing an orally administrable edible agent of aggregated substance-containing laminate film form according to the present invention includes at least five embodiments described below. A first embodiment of the producing method includes an irregular surface edible layer forming step (A), a smooth surface edible layer forming step (B), a pressure bonding step (C), a resin film delaminating step (D), a multiple edible layer pressure bonding step (E), and a resin film separating step (F) described below.

<Irregular Surface Edible Layer Forming Step (A)>

The coating liquid 58 that contains an aggregated substance such as powders, granules, fine particles, or particulates that are insoluble or difficultly soluble in a coating solvent and is stored in the dam portion 57 for supplying the coating liquid in the coating apparatus 50 (FIG. 9) is directly or indirectly coated on the resin film 52 through the clearance between the doctor roll 54 and the resin film 52 in the dam portion 57 to form an irregular surface edible layer having an irregular surface with a predetermined thickness. A height difference of the irregularities in the surface is 20 μm or more, and sometimes 30 μm or more.

In the irregular surface edible layer forming step (A), a covering layer, a support layer, or an adhesive layer may be first coated on the resin film, and the irregular surface edible layer may be formed thereon. In this case, the resin film coated with the covering layer, the support layer, or the adhesive layer may be wound up on the resin film winding shaft 56, and then mounted again to the resin film unwinding shaft 51 for repeating coating of a coating liquid containing a required ingredient.

Of course, the irregular surface edible layer may be directly disposed on the resin film to form a single edible layer.

A thickness of the edible layer formed on the surface of the resin film in one coating step is preferably 25 to 300 μm. A coating thickness in one coating step larger than 300 μm excessively increases the drying time to reduce productivity.

<Smooth Surface Edible Layer Forming Step (B)>

The coating liquid 58 stored in the dam portion 57 for supplying the coating liquid of the coating apparatus 50 is coated on a new resin film 52 different from the resin film used in the irregular surface edible layer forming step (A) through the clearance between the doctor roll 54 and the resin film 52 in the dam portion 57 to form an edible layer having a substantially smooth surface with a predetermined thickness.

The coating liquid 58 in this case is free of any aggregated substance such as powders, granules, fine particles, or particulates that are insoluble or difficultly soluble in a coating solvent, or contains particles (aggregated substance) such as titanium oxide that are insoluble in a solvent, have an extremely small particle size, and are not coagulated in the coating liquid. The "edible layer having a substantially smooth surface" in the method of the present invention covers an edible layer having a substantially smooth surface even containing a trace quantity of aggregated substance such as powders, granules, fine particles, or particulates that are insoluble or difficultly soluble in a coating solvent, and may contain an aggregated substance in an amount that does not substantially form an irregular surface in the layer. In any case, for the edible layer having the substantially smooth surface formed in the smooth surface edible layer forming step (B), a height difference of irregularities is preferably 10 μm or less, more preferably 5 μm or less. A thickness of the edible layer having the substantially smooth surface is preferably 10 μm or more, more preferably 10 to 50 μm.

Ingredients of the edible layer having the substantially smooth surface are not limited, but preferably contain an edible thermoplastic substance, and are more preferably substantially the same as ingredients except the aggregated substance contained in the "edible layer having an irregular surface" formed in the irregular surface edible layer forming step (A). The ratio of composition is preferably substantially the same as the percentage of the ingredients except the aggregated substance.

<Pressure Bonding Step (C)>

The edible layer-formed resin film formed in the irregular surface edible layer forming step (A) is mounted to the lower unwinding shaft 14 of the pressure bonding apparatus 10 (FIG. 1), the edible layer-formed resin film formed in the smooth surface edible layer forming step (B) is mounted to the upper unwinding shaft 13, the edible layers formed on the resin films are joined so that they face each other and passed through the nip between the pair of press rolls 15, 15 to pressurize the resin films at back surfaces to bond the edible layers together.

In pressurizing by the press rolls 15, 15, the press rolls 15, 15 or guide rolls in previous steps to the press rolls 15, 15 are heated by a built-in electric heater or a built-in steam heater in the rolls so that a temperature of the edible layers during pressurization is preferably 30° C. to 70° C. This temperature is a temperature slightly higher than a glass transition point of the thermoplastic edible substance of the edible layers and at which the thermoplastic edible substance reaches a rubber elastic range and is slightly softened and easily bonded. The temperature needs to be selected according to types of the resin film or types of substances used for the edible layer. An excessively high temperature should be avoided because it may cause the edible layers to be molten and flow to break a laminated structure or decompose an active ingredient, and cause volatilization and bumping of solvents in the edible layers, and an excessively low temperature may cause insufficient bonding. A pressurizing pressure by the press rolls is 0.05 to 1.5 MPa, preferably 0.1 to 0.7 MPa. An excessive pressure causes the edible layers to spread, which unpreferably affects quantitative accuracy per unit area. An excessively low pressure causes insufficient bonding.

<Resin Film Delaminating Step (D)>

Only the resin film 16a used in the smooth surface edible layer forming step (B) among the resin films on both sides of the bonded edible layers obtained in the pressure bonding step (C) is delaminated by winding up a tip of the resin film 16a on the delaminated film winding shaft 18 at the time when the resin films pass through the film delamination roll 17.

The resin film 16b retaining the bonded edible layers thus obtained is wound up on the winding shaft 19 into a roll to form a bonded edible layers-retained rolled film 20.

After the edible layers are passed through the nip between the press rolls 15, 15 and bonded together and before the resin film 16a is delaminated from the bonded edible layers, the bonded edible layers are preferably cooled to a temperature 10° C. or more lower than the temperature of the edible layers when pressurized by the press rolls 15, 15. Excessive cooling is unnecessary, and the temperature of the cooled edible layer is kept higher than 0° C., preferably higher than a normal temperature (or a room temperature). Thus, the cooling may be natural cooling by heat dissipation resulting from providing a long distance between the press rolls 15, 15 and the film delamination roll 17, or active cooling by blowing air at room temperature such as sterilized air or cooled air. This allows the resin film 16a to be reliably continuously delaminated from the intermediate compression bonded product 16.

<Multiple Edible Layer Pressure Bonding Step (E)>

The resin film retaining the bonded edible layers having a substantially smooth surface obtained in the resin film delaminating step (D) is mounted to the lower unwinding shaft 14 of the pressure bonding apparatus 10, and the rest of the resin film retaining the irregular surface edible layer having the irregular surface obtained in the irregular surface edible layer forming step (A), or a resin film retaining an edible layer having an irregular surface made of the same or different ingredient as or from that in the rest of the resin film and separately obtained in the irregular surface edible layer forming step (A) is mounted to the upper unwinding shaft 13. Then, the edible layers formed on the resin films are joined together so that they face each other, and passed through the nip between the pair of press rolls 15, 15 to pressurize the resin films at back surfaces under the same temperature and pressure conditions as in the pressure bonding step (C) to bond the edible layers together to form bonded edible layers.

In the multiple edible layer pressure bonding step (E), the edible layer-formed resin films mounted to the lower unwinding shaft 14 and the upper unwinding shaft 13 of the pressure bonding apparatus 10 may be opposite to the above described case. However, for release treatment described later for easy delamination of the resin film from the edible layer, the resin films mounted as described above are advantageous because an edible layer contact surface of the edible layer-formed resin film obtained in the resin film delaminating step (D) and mounted to the lower unwinding shaft 14 is not subjected to the release treatment, and an edible layer contact surface of the edible layer-formed resin film newly obtained on the upper unwinding shaft 13 in the irregular surface edible layer forming step (A) is subjected to the release treatment, thereby providing consistency in the entire steps from the step (A) to the step (F).

<Resin Film Separating Step (F)>

At least one resin film 16a among the resin films on both sides of the bonded edible layers obtained in the multiple edible layer pressure bonding step (E) is delaminated under the same temperature condition as in the resin film delaminating step (P) by winding up the tip of the resin film 16a on the delaminated film winding shaft 18 at the time when the resin films pass through the film delamination roll 17.

A second embodiment of a method for producing an orally administrable edible agent of aggregated substance-containing laminate film form according to the present invention includes the irregular surface edible layer forming step (A), the smooth surface edible layer forming step (B), the pressure bonding step (C), and the resin film delaminating step (D), a multiple bonded edible layers pressure bonding step (G), and a resin film separating and removing step (H) described below.

<Multiple Bonded Edible Layers Pressure Bonding Step (G)>

The resin film retaining the bonded edible layers having a substantially smooth surface obtained in the resin film delaminating step (D), and the rest of the resin film retaining the bonded edible layers having a substantially smooth surface obtained in the resin film delaminating step (D), or a resin film retaining bonded edible layers having a substantially smooth surface made of the same or different ingredient as or from that in the rest of the resin film and separately formed through the irregular surface edible layer forming step (A), the smooth surface edible layer forming step (B), the pressure bonding step (C), and the resin film delaminating step (D) are set so that one is set to the upper unwinding shaft 13 of the pressure bonding apparatus 10 in FIG. 1 and the other is set to the lower unwinding shaft 14. The bonded edible layers are joined together so that they face each other, and passed through the nip between the pair of press rolls 15, 15 to pressurize the resin films at back surfaces under the same temperature and pressure conditions as in the pressure bonding step (C) to bond the bonded edible layers together to form the bonded edible layers.

In this case, for one resin film set to the upper unwinding shaft 13 and the other resin film set to the lower unwinding shaft 14, there are a case where a covering layer, a support layer or an adhesive layer is coated on the resin film, and then the irregular surface edible layer is formed thereon (indirect coating) and a case where the irregular surface edible layer is directly formed on the resin film without forming the covering layer, the support layer or the adhesive layer (direct coating) in the irregular surface edible layer forming step (A). Even for the indirect coating, there is a case where the irregular surface edible layer is formed on the support layer in one resin film, and the irregular surface edible layer is formed on the adhesive layer in the other resin film, and so the bonded edible layers having the same multilayer structures are not always pressure bonded.

<Resin Film Separating and Removing Step (H)>

At least one resin film 16a among the resin films on both sides of the bonded edible layers obtained in the multiple bonded edible layers pressure bonding step (G) is delaminated under the same temperature condition as in the resin film delaminating step (D) by winding up the tip of the resin film 16a on the delaminated film winding shaft 18 at the time when the resin films pass through the film delamination roll 17.

A third embodiment of a method for producing an orally administrable edible agent of aggregated substance-containing laminate film form according to the present invention includes the irregular surface edible layer forming step (A), and a coating smooth surface edible layer forming step (I), a coating edible layer pressure bonding step (J), and a resin film delaminating step (K) described below.

<Coating Smooth Surface Edible Layer Forming Step (I)>

The irregular surface edible layer-formed resin film wound up on the resin film winding shaft 56 of the coating apparatus 50 obtained in the irregular surface edible layer forming step (A) is again mounted to the resin film unwinding shaft 51, and a coating liquid 58 similar to that used in the smooth surface edible layer forming step (B) in the first embodiment is stored in the dam portion 57 for supplying the coating liquid. The coating liquid 58 is coated on the irregular surface of the irregular surface edible layer-formed resin film through the clearance between the doctor roll 54 and the resin film 52 in the dam portion 57 to form an edible layer having a substantially smooth surface with a predetermined thickness, thereby forming a coating laminated edible layer having a substantially smooth surface.

For the edible layer having the substantially smooth surface coated on the irregular surface edible layer in the coating smooth surface edible layer forming step (I), a height difference of irregularities is preferably 10 µm or less, more preferably 5 µm or less. A thickness of the edible layer having the substantially smooth surface is preferably 10 µm or more, more preferably 10 to 50 µm.

Ingredients of the edible layer having the substantially smooth surface are not limited, but preferably contain an edible thermoplastic substance like the ingredients of the edible layer used in the smooth surface edible layer forming step (B) in the first embodiment, and are more preferably substantially the same as ingredients except the aggregated substance of the edible layer having the irregular surface formed in the irregular surface edible layer forming step (A). The ratio of composition is preferably substantially the same as the percentage of ingredients except the aggregated substance.

<Coating Edible Layer Pressure Bonding Step (J)>

The resin film retaining the coating laminated edible layer having a substantially smooth surface obtained in the coating smooth surface edible layer forming step (I) is mounted to the lower unwinding shaft 14 of the pressure bonding apparatus 10, and the rest of the resin film retaining the edible layer having the irregular surface obtained in the irregular surface edible layer forming step (A), or a resin film retaining an edible layer having an irregular surface made of the same or different ingredient as or from that in the rest of the resin film and separately obtained in the irregular surface edible layer forming step (A) is mounted to the upper unwinding shaft 13. Then, the edible layers formed on the resin films are joined together so that they face each other, and passed through the nip between the pair of press rolls 15, 15 to pressurize the resin films at back surfaces under completely the same temperature and pressure conditions as in the pressure bonding step (C) to bond the coating laminated edible layer and the edible layer to form the bonded edible layers.

In the coating edible layer pressure bonding step (J), as in the multiple edible layer pressure bonding step (E) in the first embodiment, the edible layer-formed resin films mounted to the lower unwinding shaft 14 and the upper unwinding shaft 13 of the pressure bonding apparatus 10 may be opposite to the above described case, and for release treatment described later for easy delamination of the resin film from the edible layer, the resin films mounted as described above is advantageous because of providing consistency in the entire steps.

<Resin Film Delaminating Step (K)>

At least one resin film 16a among the resin films on both sides of the bonded edible layers obtained in the coating edible layer pressure bonding step (J) is delaminated under the same temperature condition as in the resin film delaminating step (D) in the first embodiment by winding up the tip of the resin film 16a on the delaminated film winding shaft 18 at the time when the resin films pass through the film delamination roll 17.

A fourth embodiment of a method for producing an orally administrable edible agent of aggregated substance-containing laminate film form according to the present invention includes the irregular surface edible layer forming step (A), and the coating smooth surface edible layer forming step (I), and a multiple coating laminated edible layer pressure bonding step (L), and a resin film delaminating and removing step (M) described below.

<Multiple Coating Laminated Edible Layer Pressure Bonding Step (L)>

The resin film retaining the coating laminated edible layer having a substantially smooth surface obtained in the coating smooth surface edible layer forming step (I), and the rest of the resin film retaining the coating laminated edible layer having a substantially smooth surface obtained in the coating smooth surface edible layer forming step (I), or a resin film retaining a coating laminated edible layer having a substantially smooth surface made of the same or different ingredient as or from that in the rest of the resin film and separately formed through the irregular surface edible layer forming step (A) and the coating smooth surface edible layer forming step (I) are set so that one is set to the upper unwinding shaft 13 of the pressure bonding apparatus 10 in FIG. 1 and the other is set to the lower unwinding shaft 14. The coating laminated edible layers are joined together so that they face each other, and passed through the nip between the pair of press rolls 15, 15 to pressurize the resin films at back surfaces under the same temperature and pressure conditions as in the pressure bonding step (C) in the first embodiment to bond the coating laminated edible layers together to form the bonded edible layers.

In this case, for one resin film set to the upper unwinding shaft 13 and the other resin film set to the lower unwinding shaft 14, there are a case where a covering layer, a support layer or an adhesive layer is coated on the resin film, and then the irregular surface edible layer is coated thereon (indirect coating) and a case where the irregular surface edible layer is directly formed on the resin film without forming the covering layer, the support layer or the adhesive layer (direct coating) in the irregular surface edible layer forming step (A). Even for the indirect coating, there is a case where the irregular surface edible layer is formed on the support layer in one resin film, and the irregular surface edible layer is formed on the adhesive layer in the other resin film, and so the bonded edible layers having the same multilayer structures are not always pressure bonded, as in the multiple bonded edible layers pressure bonding step (G) in the second embodiment.

<Resin Film Delaminating and Removing Step (M)>

At least one resin film 16a among the resin films on both sides of the bonded edible layers obtained in the multiple coating laminated edible layer pressure bonding step (L) is delaminated under the same temperature condition as in the resin film delaminating step (D) in the first embodiment by winding up the tip of the resin film 16a on the delaminated film winding shaft 18 at the time when the resin films pass through the film delamination roll 17.

A fifth embodiment of a method for producing an orally administrable edible agent of aggregated substance-containing laminate film form according to the present invention includes the irregular surface edible layer forming step (A), the smooth surface edible layer forming step (B), the pressure bonding step (C), and the resin film delaminating step (D), a multiple coating bonded edible layers pressure bonding step (N), and a resin film removing step (O) described below.

<Multiple Coating Bonded Edible Layers Pressure Bonding Step (N)>

The resin film retaining the bonded edible layers having a substantially smooth surface obtained in the resin film delaminating step (D) is set to one of the upper unwinding shaft 13 and the lower unwinding shaft 14 of the pressure bonding apparatus 10 in FIG. 1.

On the other hand, the resin film retaining a coating laminated edible layer having a substantially smooth surface made of the same or different ingredient as or from the bonded edible layers in the resin film delaminating step (D) and obtained as in the coating smooth surface edible layer forming step (I) in the third embodiment is set to the other of the upper unwinding shaft 13 and the lower unwinding shaft 14 of the pressure bonding apparatus 10. Specifically, the irregular surface edible layer-formed resin film obtained in the irregular surface edible layer forming step (A) is again mounted to the resin film unwinding shaft 51 of the coating apparatus 50, and a coating liquid 58 stored in the dam portion 57 for supplying the coating liquid similar to that used in the smooth surface edible layer forming step (B) is coated on the irregular surface of the irregular surface edible layer-formed resin film through the clearance between the doctor roll 54 and the resin film 52 in the dam portion 57 to form an edible layer having a substantially smooth surface with a predetermined thickness, thereby forming a coating laminated edible layer having a substantially smooth surface with a predetermined thickness. At this time, the irregular surface edible layer-formed resin film mounted to the resin film unwinding shaft 51 may be the rest of the irregular surface edible layer-formed resin film used in the pressure bonding step (C), or a resin film retaining an edible layer having an irregular surface made of the same or different ingredient as or from that in the rest of the resin film and separately obtained in the irregular surface edible layer forming step (A).

The bonded edible layers and the coating laminated edible layers unwound from the upper unwinding shaft 13 and the lower unwinding shaft 14 of the pressure bonding apparatus 10 are joined together so that they face each other, and passed through the nip between the pair of press rolls 15, 15 to pressurize the resin films at back surfaces under the same temperature and pressure conditions as in the pressure bonding step (C) to bond the bonded edible layers and the coating laminated edible layer together to form the bonded edible layers.

In this case, for one resin film set to the upper unwinding shaft 13 and the other resin film set to the lower unwinding shaft 14, there are a case where a covering layer, a support layer or an adhesive layer is coated on the resin film, and then the irregular surface edible layer is coated thereon (indirect coating) and a case where the irregular surface edible layer is directly formed on the resin film without forming the covering layer, the support layer or the adhesive layer (direct coating) in the irregular surface edible layer forming step (A). Even for the indirect coating, there is a case where the irregular surface edible layer is formed on the support layer in one resin film, and the irregular surface edible layer is formed on the adhesive layer in the other resin film, and so the bonded edible layers and the coating laminated edible layer having the same multilayer structures are not always pressure bonded.

<Resin Film Removing Step (O)>

At least one resin film 16a among the resin films on both sides of the bonded edible layers obtained in the multiple coating bonded edible layers pressure bonding step (N) is delaminated under the same temperature condition as in the resin film delaminating step (D) by winding up the tip of the resin film 16a on the delaminated film winding shaft 18 at the time when the resin films pass through the film delamination roll 17.

The five embodiments of the method for producing an orally administrable edible agent of aggregated substance-containing laminate film form according to the present invention have been described. Briefly describing the features of the method according to the present invention, when edible layers each having irregular surface due to the presence of aggregated substance are pressure bonded with the irregular surfaces thereof facing each other, an edible layer substantially free of any aggregated substance is interposed between the edible layers. This provides an orally administrable edible agent of aggregated substance-containing laminate film form having a multilayer structure in which an edible layer substantially free of any aggregated substance is interposed between two edible layers containing an aggregated substance.

Figure 5:
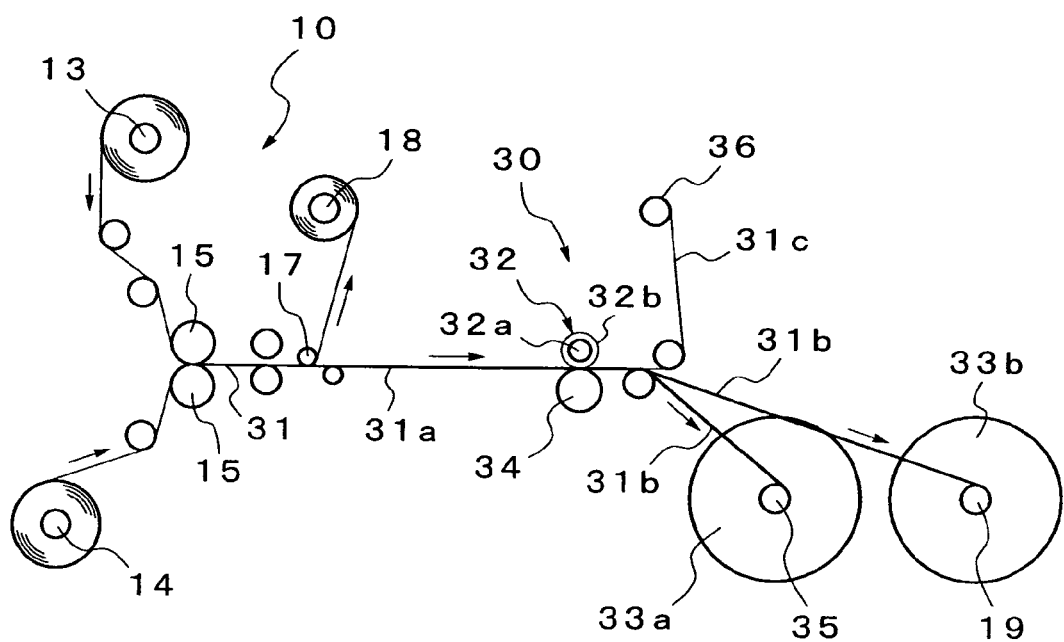
FIG. 5 illustrates an embodiment of a slitter apparatus connected to the pressure bonding apparatus in FIG. 1.

Next, steps after a final pressure bonded product retaining bonded edible layers having a desired multilayer structure is obtained by the pressure bonding apparatus 10 will be described. Specifically, the final pressure bonded product retaining an edible layer of aggregated substance-containing laminate film form obtained by the pressure bonding apparatus 10 is cut into narrow strips using a slitter apparatus 30 disposed downstream of the pressure bonding apparatus 10. Specifically, as shown in FIG. 5, a resin film on an upper surface of an intermediate pressure bonded product 31 pressured bonded by the press rolls 15, 15 is delaminated to form a final pressure bonded product 31a (in some cases, the pressure bonded product 16b in FIGS. 1 and 4 is the final pressure bonded product). The final pressure bonded product 31a (having a width of the edible layer of, for example, 460 mm) is cut into twelve narrow pressure bonded products 31b each having a width of, for example, 36 mm by a slitter 32, and the narrow pressure bonded products 31b are individually wound up on twelve reels 33a, 33b. The slitter 32 is configured so that thirteen blades 32b are arranged in parallel on an outer periphery of one roll 32a so as to circumferentially protrude. When the intermediate pressure bonded product 16 is wound up on the winding shaft 19 as shown in FIGS. 1 and 4, a gap between the slitter 32 and the roll 34 therebelow is widened, and the slitter 32 does not function. When the final pressure bonded product 31a is cut into narrow strips, the gap between the slitter 32 and the roll 34 therebelow is closed, and the final pressure bonded product 31a passed through the gap is cut into twelve narrow pressure bonded products 31b.

In the example in FIG. 5, the final pressure bonded product 31a is passed through the slitter 32 and is cut into the twelve narrow pressure bonded products 31b, and six narrow pressure bonded products 31b in an odd-numbered row are individually wound up on six reels 33a coaxially set to a product winding shaft 35 placed forward, and six narrow pressure bonded products 31b in an even-numbered row are individually wound up on six reels 33b coaxially set to the product winding shaft 19 placed backward. Cutting chips 31c at both ends of the final pressure bonded product 31a cut by the slitter 32 are wound up on a chip winding shaft 36.

Figure 6:
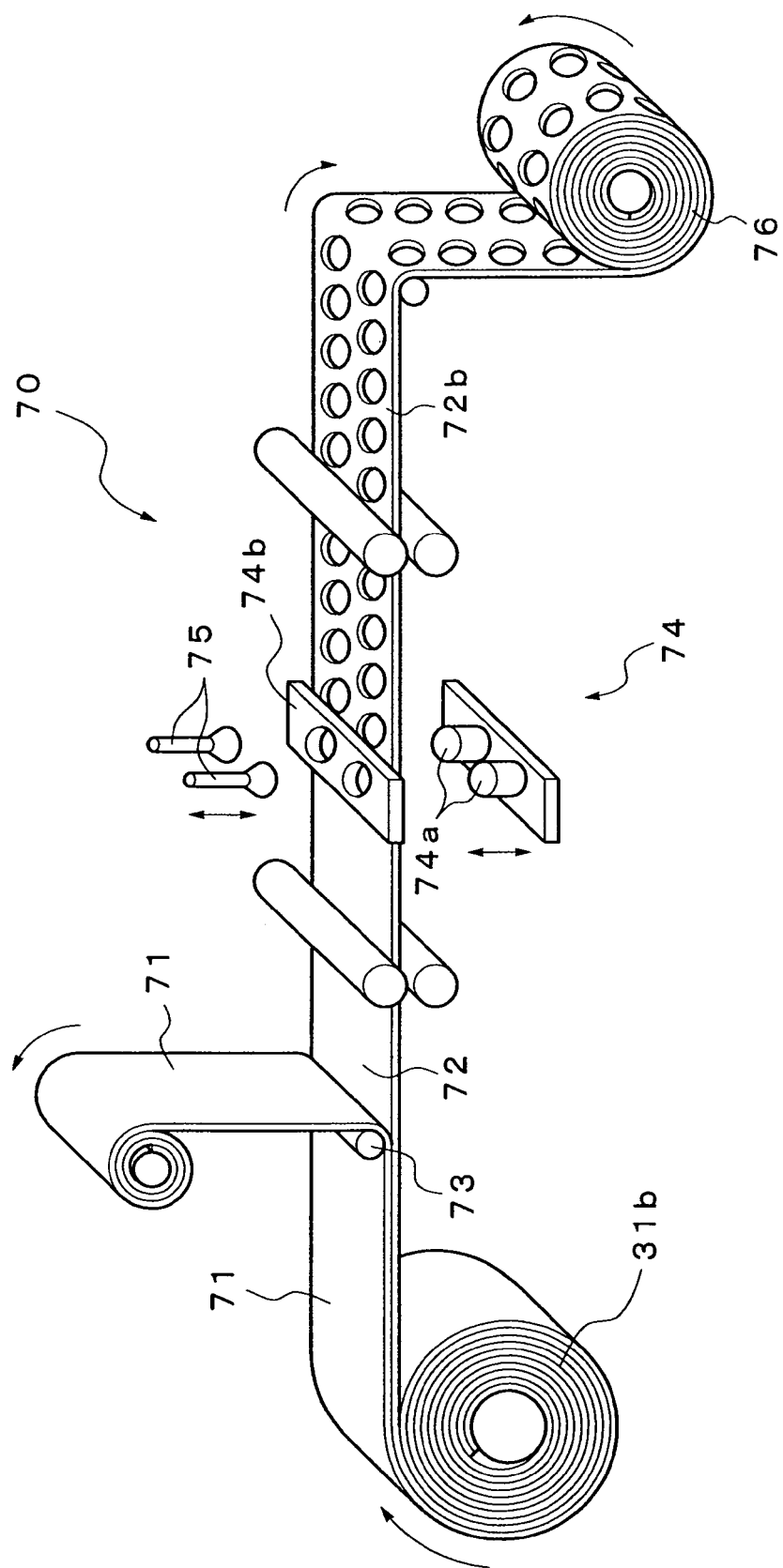
FIG. 6 is a perspective view of an embodiment of an orally administrable agent forming apparatus of a final pressure bonded product obtained by the method according to the present invention.
Figure 7:
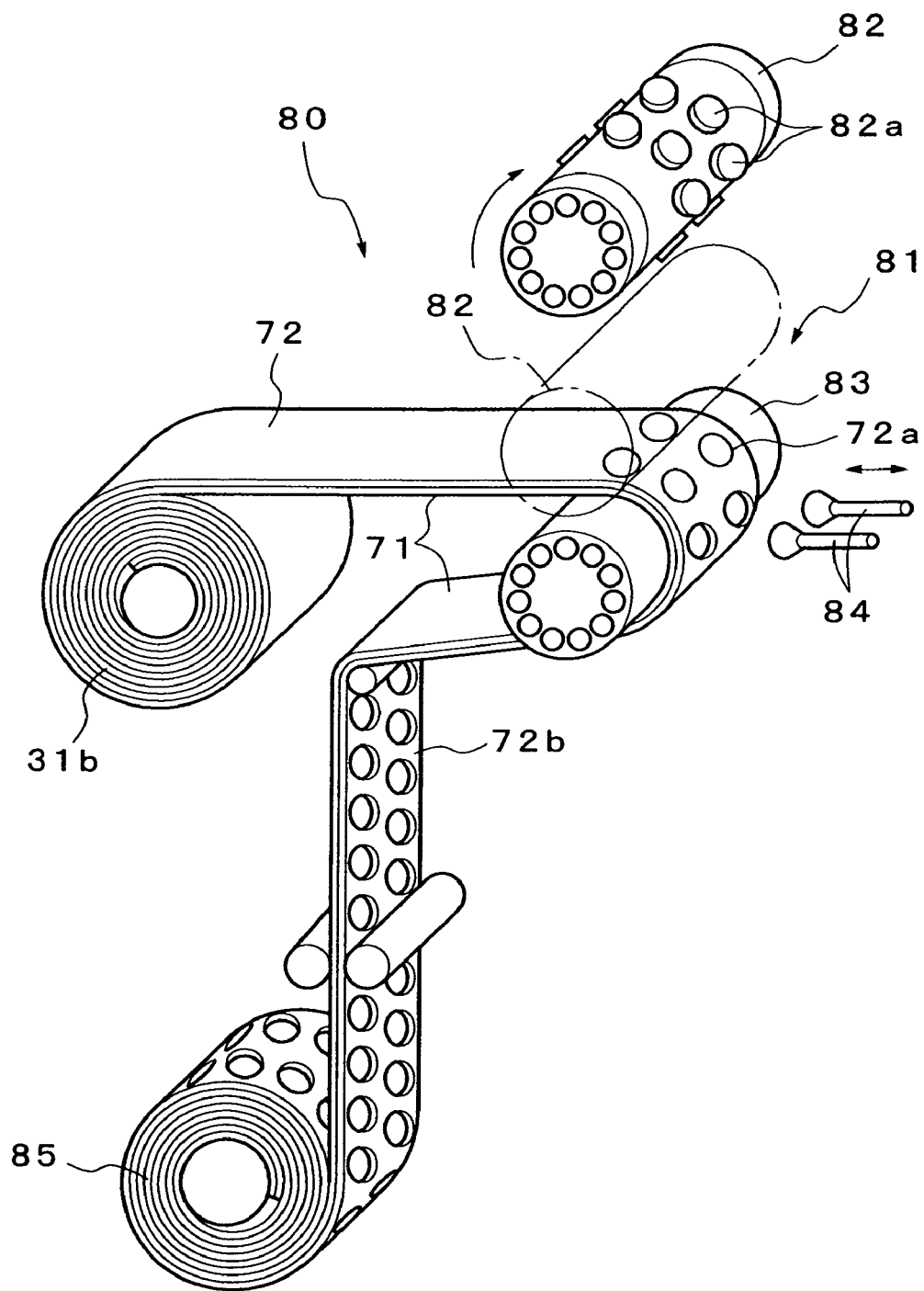
FIG. 7 is a perspective view of another embodiment of an orally administrable agent forming apparatus of a final pressure bonded product obtained by the method according to the present invention.
Figure 8:
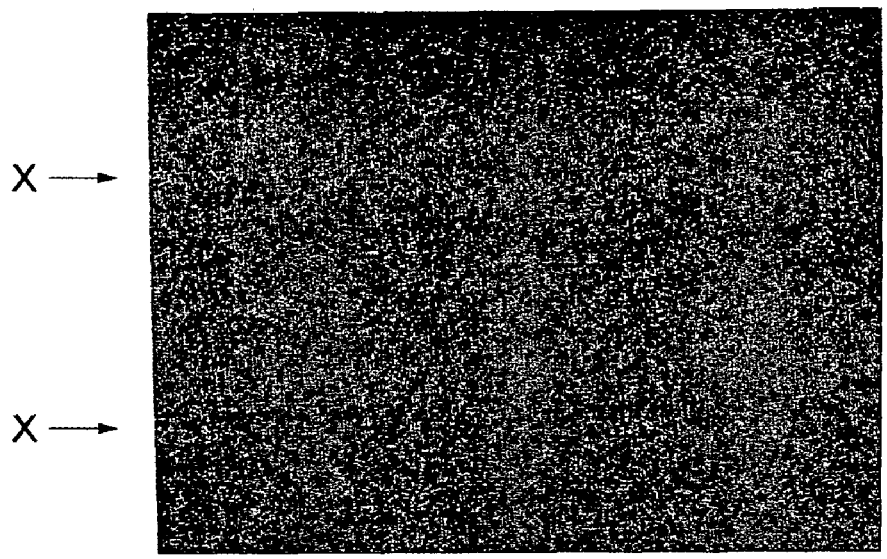
FIG. 8 is a photomicrograph (×800) showing a section of the final pressure bonded product obtained by a pressure bonding technique and a similar laminated product obtained by a conventional lamination coating technique.
Figure 8:
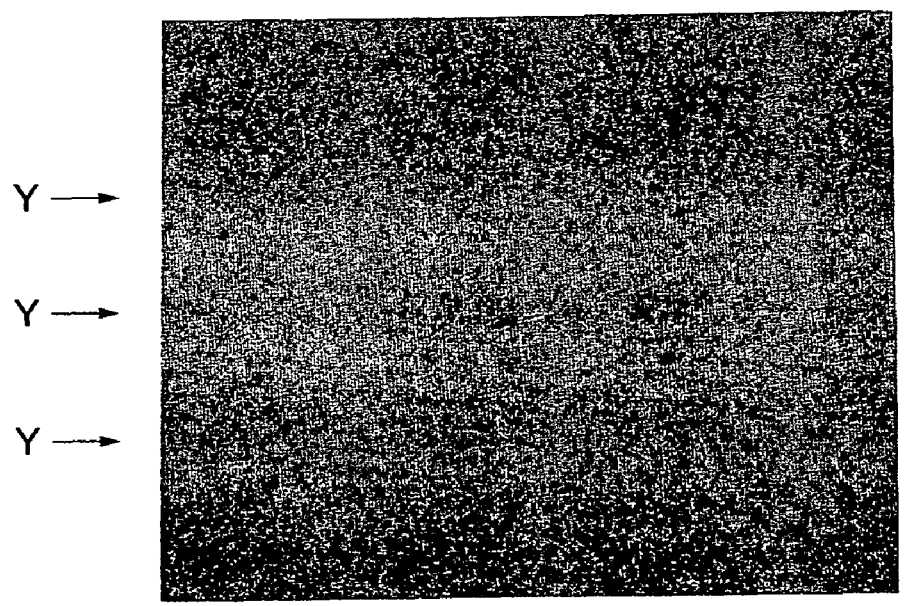

The narrow pressure bonded products 31b (36 mm width) thus cut can be formed into, for example, a circular orally administrable edible agent of aggregated substance-containing laminate film form using an orally administrable edible agent forming apparatus as shown in FIG. 6 or 7.

In an orally administrable edible agent forming apparatus 70 in FIG. 6, the narrow pressure bonded product 31b wound on the reels 33a and 33b in FIG. 5 in rolls, that is, a pressure bonded product in which one of resin films is delaminated, and bonded edible layers 72 are retained on a surface of the other resin film 71 is intermittently unwound, and the other resin film 71 is delaminated by a film delamination roll 73 to leave the bonded edible layers 72 only. Then, the bonded edible layers 72 are punched out into a circle, for example, with a diameter of 15 mm by a punching device 74. The punching device 74 includes cutting blades 74a that vertically move and a securing plate 74b having through-holes through which the cutting blades pass. When the bonded edible layers 72 intermittently moved stops at a position of the punching device 74, the cutting blades 74a move upward and pass through the through-holes in the securing plate 74b to punch out the bonded edible layers 72 into circles with the diameter of 15 mm. The circular bonded edible layers punched out are sucked by suction pads 75 disposed above the securing plate 74b, and dropped on to a conveyer (not shown) and fed to a packaging step. Bonded edible layers chips 72b after the circular bonded edible layers are removed are wound up as a chip winding roll 76.

In an orally administrable edible agent forming apparatus 80 in FIG. 7, the narrow pressure bonded product 31b wound on the reels 33a and 33b in FIG. 5 in rolls, that is, a pressure bonded product in which one of resin films is delaminated, and bonded edible layers 72 are retained on a surface of the other resin film 71 is continuously unwound and fed to a punching device 81. The punching device 81 includes a cutting blade roll 82 and an anvil roll 83. The cutting blade roll 82 is provided with circular cutting blades 82a, for example, with a diameter of 15 mm protruding from a roll outer peripheral surface that rotates. The pressure bonded product is continuously inserted into a nip between the rolls 82 and 83, and when the pressure bonded product stops with the product being sandwiched between the rolls 82 and 83, the bonded edible layers 72 only are punched out by the cutting blades 82a protruding from the cutting blade roll 82 so as not to reach a back surface of the resin film 71. A cutting depth by the cutting blade 82a can be controlled by adjusting a clearance between the cutting blade roll 82 and the anvil roll 83. In FIG. 7, the cutting blade roll 82 and the anvil roll 83 are shown as being spaced apart for the sake of clarity, but an actual cutting operation is performed with the cutting blade roll 82 being placed in a position shown by a dash-single-dot line. In the state where the bonded edible layers only are punched out by the cutting blades 82a, circular cuts 72a corresponding to the shapes of the cutting blades are merely formed in the bonded edible layers 72, and the bonded edible layers 72 remain on the surface of the resin film 71. In this state, the resin film and the bonded edible layers rotate with the rotation of the anvil roll 83, and when they move to a position where suction pads 84 are disposed, the suction pads 84 move toward the anvil roll 83 to suck the bonded edible layers 72 surrounded by the circular cuts 72a and delaminate the bonded edible layers 72 from the resin film 71. The circular bonded edible layers 72 are then dropped onto a conveyer (not shown) and fed to a packaging step. Bonded edible layer chips 72b after the circular bonded edible layers are delaminated are wound up together with the resin film 71 as a chip winding roll 85.

A final product of the orally administrable edible agent of aggregated substance-containing laminate film form produced by the orally administrable edible agent forming apparatus 70 or 80 is in a state where the resin films are delaminated from both surfaces thereof. Thus, the two resin films joined in the pressure bonding step are both finally delaminated.

However, some final products of the orally administrable edible agent of aggregated substance-containing laminate film form are of such a type that bonded edible layers with a predetermined dimension adhere to a surface of a resin film, and a person who takes the agent delaminates the bonded edible layers from the resin film. For such a final product type, only one of the two resin films joined in the pressure bonding step may be delaminated and removed.

The above description of the invention has been made taking as an example of a batch type operation in which the resin films each retaining the single or the plurality of edible layer/layers are once wound into the rolls to form the rolled film, and then the resin rolled films are pressure bonded. However, the invention may be implemented by a continuous operation in which a plurality of coating apparatuses are used and edible layer-formed resin films obtained by the coating apparatuses are pressure bonded without being formed into rolled films, or the resin film retaining the plurality of edible layers thus obtained is pressure bonded, without being formed into a rolled film, with another resin film provided with a single or a plurality of edible layer/layers.

In the pressure bonding apparatus 10, the two resin films each retaining the edible layers are pressure bonded and then one of the resin films is delaminated. For smooth delamination, it is preferable that the resin film to be delaminated is previously subjected to release treatment by coating at least a surface (a front surface) provided with the edible layer with a hydrophobic substance so that the resin film is easily delaminated from the edible layer. When the resin film retaining the edible layer is wound into a roll to form a rolled film, a resin film surface (a back surface) provided with no edible layer also comes into contact with the edible layer in the rolled state. At this time, if the back surface of the resin film is not easily delaminated from the edible layer, unwinding of the rolled film becomes difficult. For this reason, when the resin film retaining the edible layer is a rolled film, it is preferable that the resin film to be delaminated is previously subjected to release treatment on both the front surface provided with the edible layer and the opposite back surface, while it is preferable that the resin film retaining the edible layer without being delaminated is previously subjected to release treatment at least on the back surface provided with no edible layer.

The hydrophobic substance coated on the resin film in the release treatment includes silicone resin or wax (bees wax) in compliance with standards for food additives, or the resin film may be coated with metal foil such as aluminum foil or tin foil.

The resin film as a base film for retaining the edible layer may be selected from films made of resin such as polyethylene terephthalate, polyethylene naphthalate, copolymer polyester, polyimide, polypropylene, cellulose triacetate, polyvinyl acetate resin, ethylenevinyl acetate copolymer, polyethylene, polyvinyl chloride, polycarbonate, polypropylene, triacetate, fluorocarbon resin (ETFE, PFA, FEP), etc. In particular, polyethylene terephthalate (PET) may be preferably used.

The laminated structure of the orally administrable edible agent of aggregated substance-containing laminate film obtained by the present invention is not limited, and any number of layers of various types suitable for developing a desired drug effect or function may be laminated. A laminated structure of a general orally administrable agent of film form comprises a covering layer that forms an outermost layer, a drug layer that contains a base and an active ingredient of the orally administrable agent, and if required, a support layer laminated in succession. The term "edible" herein means that the agent consists of only substances accepted as food and food additives and/or drugs and pharmaceutical additives approved for oral administration, and the term "edible layer" is used as the term generally referring to an edible covering layer, an edible drug layer, and an edible support layer and the like.

The orally administrable edible agent of aggregated substance-containing laminate film form according to the present invention contains an aggregated substance such as powders, granules, fine particles, particulates insoluble or difficultly soluble in a coating solvent that form an irregular surface in an edible drug layer containing a base and an active ingredient of the orally administrable agent. As the aggregated substance, the following insoluble drugs or high crystalline drugs may be used that can be used as active ingredients having a physiological activity:

azelastine hydrochloride (allergic disease treatment drug), adenine (purine base for leukopenia), atorvastatin calcium hydrate (HMG-CoA reductase inhibitor), afloqualone (JP14) (myotonic disease treatment drug), amosulalol hydrochloride ($\alpha$1, $\beta$-blocker), aripiprazole (dopamine autoreceptor agonist: schizophrenia), arotinolol hydrochloride ($\alpha$, $\beta$-blocker), ambroxol hydrochloride (airway lubricant and expectorant), irsogladine maleate (mucosa-protecting gastritis and ulcer treatment drug), estriol (estrogenic hormone), oxazolam (benzodiazepine minor tranquilizer), carboquone (anticancer alkylating agents), candesartan cilexetil (angiotensin II receptor antagonist), quazepam (benzodiazepine sleep disorder drug), glibenclamide (sulfonylurea hypoglycemic agent), glimepiride (sulfonylurea hypoglycemic agent), clemastine fumarate (benzhydryl ether antihistamine drug), cloxazolam (minor tranquilizer), clonazepam (benzodiazepine antiepileptic drug), chlorhexidine hydrochloride (intraoral infection preventive and treatment drug), chlormadinone acetate-mestranol (estrogenic and progestational mixed hormone), santonin (lumbricide), diazepam (minor tranquilizer), digoxin (digitalis cardiac glycoside), cisapride (benzamide digestive tract motility activator), dihydroergotamine mesylate ($\alpha$-stimulant and blocker), dimemorfan phosphate (antitussive drug), zopiclone (cyclopyrrolone sleep disorder drug), tamoxifen citrate (antiestrogen), thiamin disulfide (vitamin B1 derivative), thioctic acid amide (metabolic agent), tenoxicam (oxicam analgesic and antiphlogistic drug), tripamide (vasoactive and renal active antihypertensive drug), tretinoin (vitamin A active metabolite and APL treatment drug), domperidone (gastrointestinal motility improving drug), nicardipine hydrochloride (dihydropyridine Ca antagonist), nitrazepam (benzodiazepine hypnotic), nifedipine (dihydropyridine Ca antagonist), nipradilol ($\beta$-blocker), nimetazepam (benzodiazepine insomnia treatment drug), baclofen (anticontracture GABA derivative), biotin (vitamin H), pipethanate ethobromide (anticholinergic and antispasmodic agent), biperiden (antiparkinson drug), pimozide (antipsychotic drug), piroxicam (oxicam analgesic and antiphlogistic drug), pindolol ($\beta$-blocker), famotidine (H2-receptor antagonist: gastric ulcer), bunazosin hydrochloride ($\alpha$1-blocker), bupranolol hydrochloride ($\alpha$1-blocker), prazosin hydrochloride ($\alpha$1-blocker), flunitrazepam (sleep and anaesthetic induction agent), brotizolam (thienotriazolodiazepine sleep induction agent), propagermanium (chronic hepatitis B treatment and germanium drug), bromazepam (benzodiazepine psychoneurotic drug), bromhexine hydrochloride (airway mucus dissolvent), bromperidol (butyrophenone tranquilizer), behyd RA tablets (antihypertensive agent), perphenazine (phenothiazine tranquilizer), helenien (dark adaptation improving carotenoid), benzylhydrochlorothiazide (thiazide diuretic antihypertensive drug), penbutolol sulfate ($\beta$-blocker), bopindolol malonate ($\alpha$-blocker and prodrug), mazindol (anorectic agent), manidipine hydrochloride (dihydropyridine Ca antagonist), mexazolam (oxazolobenzodiazepine antianxiety drug), mestanolone (anabolic steroid), methyclothiazide (thiazide diuretic antihypertensive drug), methylprednisolone (adrenocortical hormone), methoxsalen (vitiligo vulgaris treatment drug), methotrexate (folate metabolism antagonist and antirheumatic drug), mepitiostane (androstane renal anemia and anti-mammary tumor drug), mepenzolate bromide (irritable colon syndrome treatment anticholinergic drug), melphalan (anti-multiple myeloma alkylating agent), mosapride citrate (gastrointestinal motility accelerator), folic acid (vitamin B), riboflavin and pyridoxine hydrochloride (vitamin B2 and B6 agent), ethyl loflazepate (benzodiazepine long-acting anxiolytic drug), lormetazepam (sleep induction agent), or the like.

As aggregated substance as food that can be used as active ingredients contained in the drug layer, fiber of natural product origin such as mulberry leaves (that prevent postprandial hyperglycemia and diabetes) may be used.

As the base used with the active ingredient in the edible drug layer, the following substances may be used alone or in combination:

polyvinylpyrrolidone, polyvinyl alcohol, sodium polyacrylate; carboxymethyl cellulose, starch, xanthan gum, karaya gum, sodium alginate, methylcellulose, carboxyvinyl polymer, agar, hydroxypropyl cellulose, hydroxypropylmethylcellulose phthalate (HPMCP), cellulose acetatephthalate (CAP), carboxymethylethylcellulose (CMEC), ethylcellulose, hydroxyethylcellulose, hydroxypropylmethylcellulose, carboxyvinyl polymer (trade name: Carbopol), tragacanth, gum arabic, locust beans gum, guar gum, carrageenan, dextrin, dextran, amylose, carboxymethyl cellulose potassium, carboxymethyl cellulose sodium, carboxymethyl cellulose calcium, pullulan, chitosan, carboxymethyl starch, seed coat of plantago, galactomannan, eudragit, casein, alkyl ester alginate, or the like.

The edible covering layer provides a function of protecting a surface of the orally administrable agent of film form or a function of adhering to oral mucosa when used as a patch, and the following substances may be used alone or in combination:

polyvinylpyrrolidone, gelatin, polyvinyl alcohol, sodium polyacrylate, starch, xanthan gum, karaya gum, hydroxypropyl cellulose, water-insoluble methacrylic acid copolymer, ethyl methacrylate and trimethyl ammonium ethyl chloride methacrylate copolymer, dimethylaminoethyl methacrylate and methyl methacrylate copolymer, carboxyvinyl polymer (tradename: Carbopol), tragacanth, gum arabic, locust beans gum, guar gum, dextrin, dextran, amylose, pullulan, chitosan, casein, alkyl ester alginate, or the like.

The edible support layer is for preventing elution of the active ingredient to a non-target site in oral cavity, and the object may be achieved by using the following substances alone or in combination to form a difficultly soluble layer or an insoluble layer in the oral cavity:

gelatin, carboxymethyl cellulose, methylcellulose, carboxyvinyl polymer, agar, hydroxypropyl cellulose, hydroxy propyl methyl cellulose phthalate (HPMCP), cellulose acetate phthalate (CAP), carboxymethylethylcellulose (CMEC), ethylcellulose, hydroxyethylcellulose, hydroxypropylmethylcellulose, cellulose acetate phthalate, locust beans gum, guar gum, carrageenan, carboxymethyl cellulose potassium, carboxymethyl cellulose sodium, carboxymethyl cellulose calcium, shellac resin (shellac, white clear shellac), starch, cellulose acetate, polyvinyl alcohol, hydroxyethylmethylcellulose, carboxymethyl starch, seed coat of plantago, galactomannan, eudragit, or the like.

The orally administrable edible agent of aggregated substance-containing laminate film form obtained by the present invention preferably contains at least one substance having a thermoplastic property among the edible substances described above in each of the edible layers (the edible covering layer, drug layer, support layer, or the like) bonded together. The edible layers containing the thermoplastic substance are slightly softened by heating in the pressure bonding step and reliably bonded together. As the edible substance having an outstanding thermoplastic property, the following substances may be used, and each of the edible layers bonded together preferably contains the edible thermoplastic substance selected from the following substances alone or in combination:

amylose, carboxymethyl cellulose potassium, carboxymethyl cellulose sodium, carboxymethyl cellulose calcium, alkyl ester alginate, sodium alginate, ethylcellulose, eudragit, carboxymethylethylcellulose, carboxymethyl starch, carboxymethyl cellulose, agar, gelatin, shellac, dextran, dextrin, starch, tragacanth, hydroxyethylcellulose, hydroxypropylcellulose, hydroxypropylmethylcellulose, hydroxypropylmethylcellulose phthalate, polyvinylpyrrolidone, methacrylic acid copolymer, methylcellulose phthalate, or the like.

Dextrin and starch are edible thermoplastic substances as described above, while pullulan produced from starch does not have a thermoplastic property though it is also polysaccharide. Edible substances such as pullulan having no thermoplastic property (non-thermoplastic substances) remain powdery and are not formed into a film even if they are heated to about 70° C. and compressed. In order for each of edible layers to be bonded to contain such a non-thermoplastic substance, an edible thermoplasticity adding substance that adds a thermoplastic property to a non-thermoplastic substance is used together to allow pressure bonding of the edible layers. As edible thermoplasticity adding substances, the following substances may be used. Also in the case where each of edible layers to be bonded contains no edible thermoplastic substance, or the content thereof is low, substances selected from the following edible thermoplasticity adding substances may be preferably used alone or in combination to be contained in each of edible layers to be bonded:

polyethylene glycol (Macrogol (Japanese pharmacopoeia)), glycerine (Japanese pharmacopoeia), concentrated glycerine (Japanese pharmacopoeia), glycerine fatty acid ester, propylene glycol, dimethylpolysiloxane-silicon dioxide mixture (also known as silicone resin), karion 83 (Japanese pharmacopoeia), triethyl citrate, D-sorbitol, medium chain fatty acid triglyceride (Japanese Pharmaceutical Excipients), polyoxyethylene (105), polyoxypropylene (5) (glycol Japanese Pharmaceutical Excipients), glyceryl monostearate (Japanese pharmacopoeia), or the like. These substances may be used as plasticizers, and in particular, polyethylene glycol (Macrogol), glycerine, concentrated glycerine and propylene glycol may be preferably used.

The edible covering layer, drug layer, and support layer that are the edible layers of the orally administrable edible agent of aggregated substance-containing laminate film form obtained by the present invention may be formed by using the above described ingredient dissolved or dispersed in the following solvent to perform coating and drying in the edible layer forming step:

water, ethanol, acetic acid, acetone, anisole, 1-butanol, 2-butanol, n-butyl acetate, t-butylmethylether, cumene, dimethyl sulfoxide, ethyl acetate, diethyl ether, ethyl formate, formic acid, heptane, isobutyl acetate, isopropyl acetate, methyl acetate, 3-methyl-1-butanol, methyl ethyl ketone, methyl isobutyl ketone, 2-methyl-1-propanol, pentane, 1-pentanol, 1-propanol, 2-propanol, propyl acetate, tetrahydrofuran, acetonitrile, chlorobenzene, chloroform, cyclohexane, 1,2-dichloroethene, dichloromethane, 1,2-dimethoxyethane, N,N-dimethylacetamide, N,N-dimethylformamide, 1,4-dioxane, 2-ethoxyethanol, ethylene glycol, formamide, hexane, methanol, 2-methoxyethanol, methyl butyl ketone, methylcyclohexane, N-methylpyrrolidone, nitromethane, pyridine, sulfolane, tetralin, toluene, 1,1,2-trichloroethene, xylene, 1,1-diethoxypropane, 1,1-dimethoxymethane, 2,2-dimethoxypropane, isooctane, isopropyl ether, methylisopropylketon, methyltetrahydrofuran, petroleum ether, trichloroacetic acid, trifluoroacetic acid, methylene chloride, or the like. Among these solvents, ethanol, water, ethyl acetate, or a combination thereof (for example, ethanol-water mixture, ethanol-ethyl acetate mixture) is most preferably used.

To each edible layer of the orally administrable edible agent of aggregated substance laminate film form obtained by the present invention, edible additives may be added, if required, such as plasticizers, taste corrigents, flavor corrigents, or coloring agents. As the plasticizers, polyethylene glycol (Macrogol), glycerine (Japanese pharmacopoeia), concentrated glycerine (Japanese pharmacopoeia), propylene glycol or the like can be used. As the taste corrigents, sweeteners such as saccharin, glycyrrhizinic acid, saccharose, fructose, or mannitol, refrigerants such as menthol or peppermint oil, and organic acid compounds that provide acid taste such as citrate, tartaric acid, or fumarate, can be used. As the flavor corrigents, natural or synthetic flavor can be used. As the coloring agents, agents used in general preparations such as edible lake may be used.

EXAMPLES

Example 1

A famotidine containing rapid-soluble film preparation as an orally administrable edible agent of aggregated substance-containing laminate film form was prepared by the producing method of the present invention.

<Preparation of Covering Layer Solution>

To an appropriate amount of ethanol-water mixed solvent (containing 40 parts by weight of ethanol), 17.0 parts by weight of maltitol and 8.0 parts by weight of polyethylene glycol (Macrogol 400 (Japanese pharmacopoeia)) were added and dissolved while stirring. Then, to the resulting solution, 15.0 parts by weight of titanium oxide (average particle size 0.45 to 0.50 μm, particle size distribution 10% pass 0.21 μm, 90% pass 0.72 μm) was added and sufficiently dispersed. To the resulting solution, 60.0 parts by weight of hydroxypropylmethylcellulose (HPMC) was added and dissolved while stirring to obtain a covering layer solution.

<Preparation of Irregular Surface Edible Layer (Drug Layer) Solution>

To an appropriate amount of 100% ethanol solvent, 0.5 parts by weight of sucralose was added and dissolved while stirring. Then, to the resulting solution, 1.0 parts by weight of sucrose fatty acid ester was added and dissolved while stirring. Further, to the resulting solution, 40.0 parts by weight of famotidine (average particle size 20 to 40 μm, particle size distribution 10% pass 10 μm, 90% pass 100 μm) was added and sufficiently dispersed. To the resulting solution, 0.14 parts by weight of grapefruit oil and 0.3 parts by weight of L-menthol were added and dissolved. Then, to the resulting solution, 58.06 parts by weight of hydroxypropylcellulose (HPC) was added and dissolved while stirring to obtain a drug layer solution.

<Preparation of Smooth Surface Edible Layer Solution>

To an appropriate amount of ethanol-water mixed solvent (containing 40 parts by weight of ethanol), 29.1 parts by weight of trehalose and 0.5 parts by weight of sucralose were added and dissolved while stirring. Then, to the resulting solution, 0.1 parts by weight of grapefruit oil and 0.3 parts by weight of L-menthol were added and dissolved. To the resulting solution, 70.0 parts by weight of hydroxypropylcellulose (HPC) was added and dissolved while stirring to obtain a smooth surface edible layer solution.

<Irregular Surface Edible Layer Forming Step (A)>

On the unwinding shaft 51 of the coating apparatus 50 in FIG. 9, a polyethylene terephthalate film (PET film) whose back surface was subjected to silicone release treatment was set, and the covering layer solution was supplied to the dam portion 57 to coat the covering layer solution on a front surface (a surface that is not subjected to the silicone release treatment) of the PET film, and then dried at a drying temperature of 70° C. to form an edible covering layer of 15 μm thick.

The PET film provided with the covering layer was again set to the unwinding shaft 51, and the drug layer solution was coated on the covering layer, and dried at a drying temperature of 70° C. to form a drug layer of 40 μm thick having an irregular surface (55 μm in two layers) (intermediate product (a)).

The irregularities in the intermediate product (a) were measured by a digital thickness gauge SMD-565 (produced by TECLOCK) to recognize that a height difference of the irregularities was 20 μm at the highest.

<Smooth Surface Edible Layer Forming Step (B)>

On the unwinding shaft 51 of the coating apparatus 50 in FIG. 9, a PET film different from the one used in the irregular surface edible layer forming step (A), whose both surfaces were subjected to silicone release treatment, was set, and the smooth surface edible layer solution was supplied to the dam portion 57 to coat the smooth surface edible layer solution on a surface of the PET film, and then dried at a drying temperature of 70° C. to form an edible layer of 15 μm thick having a smooth surface (intermediate product (b)).

<Pressure Bonding Step (C)>

The intermediate product (b) wound in the roll was set to the upper unwinding shaft 13 of the pressure bonding apparatus 10 in FIG. 1, and the intermediate product (a) wound in the roll was set to the lower unwinding shaft 14. The edible layer having the irregular surface of the intermediate product (a) and the edible layer having the smooth surface of the intermediate product (b) that were unwound were introduced into the nip between the pair of press rolls 15, 15 so that they face each other, and bonded together at a pressure bonding temperature of 40° C. and a pressure of 1.0 MPa and laminated.

<Resin Film Delaminating Step (D)>

The PET film of the intermediate product (b) only located on an upper surface of an intermediate pressure bonded product after passing through the press rolls 15, 15 was drawn along the peripheral surface of the film delamination roll 17, wound up on the delaminated film winding shaft 18 and delaminated from the intermediate pressure bonded product, and then the intermediate pressure bonded product (intermediate product (c)) was wound up on the winding shaft 19 into a roll. The temperature of the intermediate pressure bonded product when the PET film was delaminated was 30° C. by natural heat dissipation.

<Multiple Edible Layers Pressure Bonding Step (E)>

After the resin film delaminating step (D), the obtained intermediate product (c) (comprising bonded edible layers consisting of three layers: the covering layer, the drug layer, and the smooth surface layer formed on the PET film) wound in the roll was set to the upper unwinding shaft 13 of the pressure bonding apparatus 10 in FIG. 1. The remainder of the intermediate product (a) (comprising an edible layer consisting of the covering layer and the drug layer formed on the PET film) wound in the roll remains on the lower unwinding shaft 14.

In this state, the bonded edible layers having a smooth surface of the intermediate product (c) and the edible layer having the irregular surface of the intermediate product (a) that were unwound were introduced into the nip between the pair of press rolls 15, 15 so that they face each other, and were bonded together under the same temperature and pressure conditions as in the pressure bonding step (C) and laminated.

<Resin Film Separating Step (F)>

The PET film of the intermediate product (c) only located on an upper surface of an intermediate pressure bonded product after passing through the press rolls 15, 15 was drawn along the peripheral surface of the film delamination roll 17, wound up on the delaminated film winding shaft 18 and delaminated from the intermediate pressure bonded product, and then the intermediate pressure bonded product (intermediate product (d)) (consisting of five layers: the covering layer, the drug layer, the smooth surface layer, the drug layer, and the covering layer laminated on the PET film) was wound up on the winding shaft 19 into a roll. The temperature at the delamination was the same as in the resin film delaminating step (D).

<Product Forming Step>

A famotidine containing rapid-soluble film preparation was obtained by a method of punching out the laminated edible layer only from the laminated product of aggregated substance-containing film form obtained as the intermediate product (d), with a blade of 14×20 mm (with a corner having a radius of 3 mm), so as not to reach the back surface of the PET film (see FIG. 7), or by a method of delaminating the PET film on the back surface from the laminated product of aggregated substance-containing film form obtained as the intermediate product (d) to obtain the laminated edible layer only, and then punching out the laminated edible layer with a rounded rectangular blade (see FIG. 6). Table 1 shows the ratio of ingredients.

TABLE 1

| Layer | Ingredient | Amount relative to the amount of solid gram of each layer [g] | Content in one piece of preparation [mg] |
|---|---|---|---|
| Covering layer | HPMC | 60 | 6.0 |
| | Titanium oxide | 15 | 1.5 |
| | Maltitol | 17 | 1.7 |
| | Macrogol 400 | 8 | 0.8 |
| | Subtotal | 100 | 10 |
| Drug layer | Famotidine | 40 | 10 |
| | HPC | 58.06 | 14.515 |
| | Sucrose fatty acid ester | 1 | 0.25 |
| | Sucralose | 0.5 | 0.125 |
| | Grapefruit oil | 0.14 | 0.035 |
| | L-menthol | 0.3 | 0.075 |
| | Subtotal | 100 | 25 |
| Smooth surface edible layer | HPC | 70 | 3.5 |
| | Trehalose | 29.1 | 1.455 |
| | Sucralose | 0.5 | 0.025 |
| | Grapefruit oil | 0.1 | 0.005 |
| | L-menthol | 0.3 | 0.015 |
| | Subtotal | 100 | 5 |

HPMC: hydroxypropylmethylcellulose
HPC: hydroxypropylcellulose

Comparative Example 1

An attempt was made to prepare a famotidine containing rapid-soluble film preparation by a producing method described below without forming a smooth surface edible layer.

<Preparation of Covering Layer Solution>

To an appropriate amount of ethanol-water mixed solvent (containing 40 parts by weight of ethanol), 17.0 parts by weight of maltitol and 8.0 parts by weight of polyethylene glycol (Macrogol 400 (Japanese pharmacopoeia)) were added and dissolved while stirring. Then, to the resulting solution, 15.0 parts by weight of titanium oxide (average particle size 0.45 to 0.50 μm, particle size distribution 10% pass 0.21 μm, 90% pass 0.72 μm) was added and sufficiently dispersed. To the resulting solution, 60.0 parts by weight of hydroxypropylmethylcellulose (HPMC) was added and dissolved while stirring to obtain a covering layer solution.

<Preparation of Irregular Surface Edible Layer (Drug Layer) Solution>

To an appropriate amount of 100% ethanol solvent, 0.5 parts by weight of sucralose was added and dissolved while stirring. Then, to the resulting solution, 1.0 parts by weight of sucrose fatty acid ester was added and dissolved while stirring. Further, to the resulting solution, 25.0 parts by weight of famotidine (average particle size 20 to 40 μm, particle size distribution 10% pass 10 μm, 90% pass 100 μm) was added and sufficiently dispersed. To the resulting solution, 0.12 parts by weight of grapefruit oil and 0.3 parts by weight of L-menthol was added and dissolved. Then, to the resulting solution, 73.06 parts by weight of hydroxypropylcellulose (HPC) was added and dissolved while stirring to obtain a drug layer solution.

<Irregular Surface Edible Layer Forming Step>

On the unwinding shaft 51 of the coating apparatus 50 in FIG. 9, a PET film whose back surface was subjected to silicone release treatment was set, and the covering layer solution was supplied to the dam portion 57 to coat the covering layer solution on a front surface (a surface that is not subjected to the silicone release treatment) of the PET film, and then dried at a drying temperature of 70° C. to form an edible covering layer of 15 μm thick.

The PET film provided with the covering layer was again set to the unwinding shaft 51, and the drug layer solution was coated on the covering layer, and dried at a drying temperature of 70° C. to form a drug layer of 65 μm thick having an irregular surface (80 μm in two layers) (intermediate product (a)). The irregularities in the intermediate product (a) were measured by a digital thickness gauge SMD-565 (produced by TECLOCK) to recognize that a height difference of the irregularities was 20 μm at the highest.

<Pressure Bonding and Resin Film Delaminating Step>

The intermediate products (a) wound in the rolls were set to the upper unwinding shaft 13 and the lower unwinding shaft 14 of the pressure bonding apparatus 10 in FIG. 1. The edible layers having irregular surfaces of the unwound intermediate products (a) were introduced into the nip between the pair of press rolls 15, 15 so that they face each other, and were bonded together at a pressure bonding temperature of 40° C. and a pressure of 1.0 MPa and laminated.

An attempt was made to draw the PET film only located on an upper surface of the bonded edible layers that reach 30° C. by natural heat dissipation after passing through the press rolls 15, 15 along the peripheral surface of the film delamination roll 17, wind up the PET film on the delaminated film winding shaft 18 to be delaminated from the bonded edible layers, and then wind up the PET film retaining the bonded edible layers on the winding shaft 19 into a roll. However, the bonded edible layers were separated into their original states on the delamination roll 17, the covering layer and the drug layer before pressure bonding were still retained on the resin film 16a wound up on the delaminated film winding shaft 18, and the covering layer and the drug layer before pressure bonding were also still retained on the resin film 16b wound up on the winding shaft 19, and thus the layers cannot be pressure bonded.

Table 2 shows the ratio of ingredients of the preparation.

TABLE 2

| Layer | Ingredient | Amount relative to the amount of solid gram of each layer [g] | Content in one piece of preparation [mg] |
|---|---|---|---|
| Covering layer | HPMC | 60 | 6.0 |
| | Titanium oxide | 15 | 1.5 |
| | Maltitol | 17 | 1.7 |
| | Macrogol 400 | 8 | 0.8 |
| | Subtotal | 100 | 10 |
| Drug layer | Famotidine | 25 | 10 |
| | HPC | 73.08 | 29.232 |
| | Sucrose fatty acid ester | 1 | 0.4 |
| | Sucralose | 0.5 | 0.2 |
| | Grapefruit oil | 0.12 | 0.048 |
| | L-menthol | 0.3 | 0.12 |
| | Subtotal | 100 | 40 |

HPMC: Hydroxypropylmethylcellulose
HPC: Hydroxypropylcellulose

Example 2

An aripiprazole containing rapid-soluble film preparation as an orally administrable edible agent of aggregated substance-containing laminate film form was prepared by the producing method of the present invention.

<Preparation of Covering Layer Solution>

To an appropriate amount of ethanol-water mixed solvent (containing 40 parts by weight of ethanol), 17.0 parts by weight of maltitol, 8.0 parts by weight of polyethylene glycol (Macrogol 400 (Japanese pharmacopoeia)), and 0.1 parts by weight of food red No. 1 were added and dissolved while stirring. Then, to the resulting solution, 14.9 parts by weight of titanium oxide (average particle size 0.45 to 0.50 μm, particle size distribution 10% pass 0.21 μm, 90% pass 0.72 μm) was added and sufficiently dispersed. To the resulting solution, 60.0 parts by weight of hydroxypropylmethylcellulose (HPMC) was added and dissolved while stirring to obtain a covering layer solution.

<Preparation of Irregular Surface Edible Layer (Drug Layer) Solution>

To an appropriate amount of 100% ethanol solvent, 2.0 parts by weight of saccharin sodium was added and dissolved while stirring. Then, to the resulting solution, 60.0 parts by weight of aripiprazole (average particle size 21.7 μm, particle size distribution 90% pass particle size 45.1 μm) was added and sufficiently dispersed. To the resulting solution, 0.14 parts by weight of cherry oil and 0.3 parts by weight of L-menthol was added and dissolved. Then, to the resulting solution, 37.56 parts by weight of hydroxypropylcellulose (HPC) was added and dissolved while stirring to obtain a drug layer solution.

<Preparation of Smooth Surface Edible Layer Solution>

To an appropriate amount of ethanol-water mixed solvent (containing 40 parts by weight of ethanol), 27.6 parts by weight of trehalose and 2.0 parts by weight of saccharin sodium were added and dissolved while stirring. Then, to the resulting solution, 0.1 parts by weight of cherry oil and 0.3 parts by weight of L-menthol were added and dissolved. To the resulting solution, 70.0 parts by weight of hydroxypropylcellulose (HPC) was added and dissolved while stirring to obtain a smooth surface edible layer solution.

<Irregular Surface Edible Layer Forming Step (A)>

On the unwinding shaft 51 of the coating apparatus 50 in FIG. 9, a polyethylene terephthalate film (PET film) whose back surface was subjected to silicone release treatment was set, and the covering layer solution was supplied to the dam portion 57 to coat the covering layer solution on a front surface (a surface that is not subjected to the silicone release treatment) of the PET film, and then dried at a drying temperature of 70° C. to form an edible covering layer of 15 μm thick.

The PET film provided with the covering layer was again set to the unwinding shaft 51, and the drug layer solution was coated on the covering layer, and dried at a drying temperature of 70° C. to form a drug layer of 40 μm thick having an irregular surface (55 μm in two layers) (intermediate product (a)).

The irregularities in the intermediate product (a) were measured by a digital thickness gauge SMD-565 (produced by TECLOCK) to recognize that a height difference of the irregularities was 20 μm at the highest.

<Smooth Surface Edible Layer Forming Step (B)>

On the unwinding shaft 51 of the coating apparatus 50 in FIG. 9, a PET film different from the one used in the irregular surface edible layer forming step (A), whose both surfaces were subjected to silicone release treatment, was set, and the smooth surface edible layer solution was supplied to the dam portion 57 to coat the smooth surface edible layer solution on a surface of the PET film, and then dried at a drying temperature of 70° C. to form an edible layer of 15 μm thick having a smooth surface (intermediate product (b)).

<Pressure Bonding Step (C)>

The intermediate product (b) wound in the roll was set to the upper unwinding shaft 13 of the pressure bonding apparatus 10 in FIG. 1, and the intermediate product (a) wound in the roll was set to the lower unwinding shaft 14. The edible layer having an irregular surface of the intermediate product (a) and the edible layer having a smooth surface of the intermediate product (b) that were unwound were introduced into the nip between the pair of press rolls 15, 15 so that they face each other, and were bonded together at a pressure bonding temperature of 40° C. and a pressure of 1.0 MPa and laminated.

<Resin Film Delaminating Step (D)>

The PET film of the intermediate product (b) only located on an upper surface of an intermediate pressure bonded product after passing through the press rolls 15, 15 was drawn along the peripheral surface of the film delamination roll 17, wound up on the delaminated film winding shaft 18 and delaminated from the intermediate pressure bonded product, and then the intermediate pressure bonded product (intermediate product (c)) was wound up on the winding shaft 19 into a roll. The temperature of the intermediate pressure bonded product when the PET film was delaminated was 30° C. by natural heat dissipation.

<Multiple Edible Layers Pressure Bonding Step (E)>

After the resin film delaminating step (D), the obtained intermediate product (c) (comprising bonded edible layers consisting of three layers: the covering layer, the drug layer, and the smooth surface layer formed on the PET film) wound in the roll was set to the upper unwinding shaft 13 of the pressure bonding apparatus 10 in FIG. 1. The remainder of the intermediate product (a) (comprising an edible layer consisting of the covering layer and the drug layer coated on the PET film) wound in the roll remains on the lower unwinding shaft 14.

In this state, the bonded edible layers having a smooth surface of the intermediate product (c) and the edible layer having the irregular surface of the intermediate product (a) that were unwound were introduced into the nip between the pair of press rolls 15, 15 so that they face each other, and bonded together under the same temperature and pressure conditions as in the pressure bonding step (C) and laminated.

<Resin Film Separating Step (F)>

The PET film of the intermediate product (c) only located on an upper surface of an intermediate pressure bonded product after passing through the press rolls 15, 15 was drawn along the peripheral surface of the film delamination roll 17, wound up on the delaminated film winding shaft 18 and delaminated from the intermediate pressure bonded product, and then the intermediate pressure bonded product (intermediate product (d)) (consisting of five layers: the covering layer, the drug layer, the smooth surface layer, the drug layer, and the covering layer laminated on the PET film) was wound up on the winding shaft 19 into a roll. The temperature at the delamination was the same as in the resin film delaminating step (D).

<Product Forming Step>

An aripiprazole containing rapid-soluble film preparation was obtained by a method of punching out the laminated edible layer only from the laminated product of aggregated substance-containing film form obtained as the intermediate product (d), with a blade of 14×20 mm (with a corner having a radius of 3 mm), so as not to reach the back surface of the PET film (see FIG. 7), or a method of delaminating the PET film on the back surface from the laminated product of aggregated substance-containing film form obtained as the intermediate product (d) to obtain the laminated edible layer only, and then punching out the laminated edible layer with a rounded rectangular blade (see FIG. 6). Table 3 shows the ratio of ingredients.

TABLE 3

| Layer | Ingredient | Amount relative to the amount of solid gram of each layer [g] | Content in one piece of preparation [mg] |
|---|---|---|---|
| Covering layer | HPMC | 60 | 6.0 |
| | Titanium oxide | 14.9 | 1.49 |
| | Food red No. 1 | 0.1 | 0.01 |
| | Maltitol | 17 | 1.7 |
| | Macrogol 400 | 8 | 0.8 |
| | Subtotal | 100 | 10 |
| Drug layer | Aripiprazole | 60 | 15 |
| | HPC | 37.56 | 9.39 |
| | Saccharin sodium | 2 | 0.5 |
| | Cherry oil | 0.14 | 0.035 |
| | L-menthol | 0.3 | 0.075 |
| | Subtotal | 100 | 25 |
| Smooth surface edible layer | HPC | 70 | 3.5 |
| | Trehalose | 27.6 | 1.38 |
| | Saccharin sodium | 2 | 0.1 |
| | Cherry oil | 0.1 | 0.005 |
| | L-menthol | 0.3 | 0.015 |
| | Subtotal | 100 | 5 |

HPMC: hydroxypropylmethylcellulose
HPC: hydroxypropylcellulose

Comparative Example 2

An attempt was made to prepare an aripiprazole containing rapid-soluble film preparation by a producing method described below without forming a smooth surface edible layer.

<Preparation of Covering Layer Solution>

To an appropriate amount of ethanol-water mixed solvent (containing 40 parts by weight of ethanol), 17.0 parts by weight of maltitol, 8.0 parts by weight of polyethylene glycol (Macrogol 400 (Japanese pharmacopoeia)), and 0.1 parts by weight of food red No. 1 were added and dissolved while stirring. Then, to the resulting solution, 14.9 parts by weight of titanium oxide (average particle size 0.45 to 0.50 μm, particle size distribution 10% pass 0.21 μm, 90% pass 0.72 μm) was added and sufficiently dispersed. To the resulting solution, 60.0 parts by weight of hydroxypropylmethylcellulose (HPMC) was added and dissolved while stirring to obtain a covering layer solution.

<Preparation of Irregular Surface Edible Layer (Drug Layer) Solution>

To an appropriate amount of 100% ethanol solvent, 2.0 parts by weight of saccharin sodium was added and dissolved while stirring. Then, to the resulting solution, 37.5 parts by weight of aripiprazole (average particle size 21.7 μm, particle size distribution 90% pass particle size 45.1 μm) was added and sufficiently dispersed. To the resulting solution, 0.12 parts by weight of cherry oil and 0.3 parts by weight of L-menthol was added and dissolved. Then, to the resulting solution, 60.08 parts by weight of hydroxypropylcellulose (HPC) was added and dissolved while stirring to obtain a drug layer solution.

<Irregular Surface Edible Layer Forming Step>

On the unwinding shaft 51 of the coating apparatus 50 in FIG. 9, a PET film whose back surface was subjected to silicone release treatment was set, and the covering layer solution was supplied to the dam portion 57 to coat the covering layer solution on a front surface (a surface that is not subjected to the silicone release treatment) of the PET film, and then dried at a drying temperature of 70° C. to form an edible covering layer of 15 μm thick.

The PET film provided with the covering layer was again set to the unwinding shaft 51, and the drug layer solution was coated on the covering layer, and dried at a drying temperature of 70° C. to form a drug layer of 65 μm thick having an irregular surface (80 μm in two layers) (intermediate product (a)). The irregularities in the intermediate product (a) were measured by a digital thickness gauge SMD-565 (produced by TECLOCK) to recognize that a height difference of the irregularities was 20 μm at the highest.

<Pressure Bonding and Resin Film Delaminating Step>

The intermediate products (a) wound in the rolls were set to the upper unwinding shaft 13 and the lower unwinding shaft 14. The edible layers having irregular surfaces of the unwound intermediate products (a) were introduced into the nip between the pair of press rolls 15, 15 so that they face each other, and bonded together at a pressure bonding temperature of 40° C. and a pressure of 1.0 MPa and laminated.

An attempt was made to draw the PET film only located on an upper surface of the bonded edible layers that reach 30° C. by natural heat dissipation after passing through the press rolls 15, 15 along the peripheral surface of the film delamination roll 17, wind up the PET film on the delaminated film winding shaft 18 to be delaminated from the bonded edible layers, and then wind up the PET film retaining the bonded edible layers on the winding shaft 19 into a roll. However, the bonded edible layers were separated into their original states on the delamination roll 17, the covering layer and the drug layer before pressure bonding were still retained on the resin film 16a wound up on the delaminated film winding shaft 18, and the covering layer and the drug layer before pressure bonding were also still retained on the resin film 16b wound up on the winding shaft 19, and thus the layers cannot be pressure bonded.

Table 4 shows the ratio of ingredients of the preparation.

TABLE 4

| Layer | Ingredient | Amount relative to the amount of solid gram of each layer [g] | Content in one piece of preparation [mg] |
|---|---|---|---|
| Covering layer | HPMC | 60 | 6.0 |
| | Titanium oxide | 14.9 | 1.49 |
| | Food red No. 1 | 0.1 | 0.01 |
| | Maltitol | 17 | 1.7 |
| | Macrogol 400 | 8 | 0.8 |
| | Subtotal | 100 | 10 |
| Drug layer | Aripiprazole | 37.5 | 15 |
| | HPC | 60.08 | 24.032 |
| | Saccharin sodium | 2 | 0.8 |
| | Cherry oil | 0.12 | 0.048 |
| | L-menthol | 0.3 | 0.12 |
| | Subtotal | 100 | 40 |

HPMC: Hydroxypropylmethylcellulose
HPC: Hydroxypropylcellulose

Example 3

A mulberry leaf containing sustained release food sheet as an orally administrable edible agent of aggregated substance-containing laminate film form was prepared by the producing method of the present invention.

<Preparation of Covering Layer Solution>

To an appropriate amount of water, 15.0 parts by weight of concentrated glycerine was added and stirred. In addition, to a small amount of ethanol, 1.0 parts by weight of sucrose fatty acid ester was added and dissolved while stirring, and the resulting solution was added to the foregoing glycerine aqueous solution. To the resulting solution, 84.0 parts by weight of pullulan was added and dissolved while stirring to obtain a covering layer solution.

<Preparation of Irregular Surface Edible Layer (Drug Layer) Solution>

To an appropriate amount of water, 5.0 parts by weight of trehalose was added and dissolved while stirring. Then, to the resulting solution, 9.9 parts by weight of concentrated glycerine was added and stirred. In addition, 25.0 parts by weight of mulberry leaf powder (average particle size 20 to 30 μm, particle size distribution 99 μm all pass), 35.0 parts by weight of α-starch, 25.0 parts by weight of enzyme denatured starch, and 0.1 parts by weight of sucralose were sufficiently mixed. The sufficiently mixed powder was added to the foregoing aqueous solution, and mixed while stirring to obtain a drug layer solution.

<Preparation of Smooth Surface Edible Layer Solution>

To an appropriate amount of water, 5.0 parts by weight of trehalose was added and dissolved while stirring. Then, to the resulting solution, 9.9 parts by weight of concentrated glycerine was added and stirred. In addition, 35.0 parts by weight of α-starch, 50.0 parts by weight of enzyme denatured starch, and 0.1 parts by weight of sucralose were sufficiently mixed. The sufficiently mixed powder was added to the foregoing solution, and dissolved while stirring to obtain a smooth surface edible layer solution.

<Irregular Surface Edible Layer Forming Step (A)>

On the unwinding shaft 51 of the coating apparatus 50 in FIG. 9, a polyethylene terephthalate film (PET film) whose back surface was subjected to silicone release treatment was set, and the covering layer solution was supplied to the dam portion 57 to coat the covering layer solution on a front surface (a surface that is not subjected to the silicone release treatment) of the PET film, and then dried at a drying temperature of 80° to form an edible covering layer of 32 μm thick.

The PET film provided with the covering layer was again set to the unwinding shaft 51, and the drug layer solution was coated on the covering layer, and dried at a drying temperature of 80° to form a drug layer of 45 μm thick having an irregular surface (77 μm in two layers) (intermediate product (a)).

The irregularities in the intermediate product (a) were measured by a digital thickness gauge SMD-565 (produced by TECLOCK) to recognize that a height difference of the irregularities was 20 μm at the highest.

<Coating Smooth Surface Edible Layer Forming Step (I)>

The PET film provided with an edible layer consisting of two layers: the covering layer and the drug layer, and having an irregular surface of the intermediate product (a) was again set to the unwinding shaft 51, and the smooth surface edible layer solution was coated on the drug layer, and then dried at a drying temperature of 80° to form an edible layer of 27 μm thick having a smooth surface (104 μm in three layers) (intermediate product (b)).

<Multiple Coating Laminated Edible Layer Pressure Bonding Step (L)>

The intermediate products (b) (comprising edible layers consisting of three layers: the covering layer, the drug layer, and the smooth surface layer coated on the PET film) wound in the roll were set to the upper unwinding shaft 13 and the lower unwinding shaft 14 of the pressure bonding apparatus 10 in FIG. 1. The edible layers having the smooth surfaces of the unwound intermediate product (b) were introduced into the nip between the pair of press rolls 15, 15 so that they face each other, and bonded together at pressure bonding temperature of 40° C. and a pressure of 1.0 MPa and laminated.

<Resin Film Delaminating and Removing Step (M)>

The PET film only located on an upper surface of the bonded edible layers that reach 30° C. by natural heat dissipation after passing through the press rolls 15, 15 was drawn along the peripheral surface of the film delamination roll 17, wound up on the delaminated film winding shaft 18 to be delaminated from the bonded edible layers, and the PET film retaining the bonded edible layers was wound up on the winding shaft 19 into a roll (intermediate product (c)).

<Bonded Multiple Edible Layer Pressure Bonding Step>

After the resin film delaminating and removing step (M), the obtained intermediate products (c) (comprising edible layers consisting of six layers: the covering layer, the drug layer, the smooth surface layer, the smooth surface layer, the drug layer, and the covering layer laminated on the PET film) wound in the roll were set to the upper unwinding shaft 13 and the lower unwinding shaft 14 of the pressure bonding apparatus 10 in FIG. 1.

In this state, the bonded multiple edible layers were introduced into the nip between the pair of press rolls 15, 15 so that the covering layers having smooth surfaces of the unwound intermediate product (c) face each other, and bonded together under the same temperature and pressure conditions as in the multiple coating laminated edible layer pressure bonding step (L) and laminated.

<Resin Film Separating Step>

The PET film of the intermediate product (c) only located on an upper surface of an intermediate pressure bonded product after passing through the press rolls 15, 15 was drawn along the peripheral surface of the film delamination roll 17, wound up on the delaminated film winding shaft 18 and delaminated from the intermediate pressure bonded product, and then the intermediate pressure bonded product (intermediate product (d)) was wound up on the winding shaft 19 into a roll. The temperature at the delamination was substantially the same as in the resin film delaminating and removing step (M).

<Product Forming Step>

A mulberry leaf containing sustained release food sheet was obtained by a method of punching out the laminated edible layer only from the orally administrable edible agent of aggregated substance-containing laminate film form obtained as the intermediate product (d) (an intermediate pressure bonded product consisting of twelve layers: the covering layer, the drug layer, the smooth surface layer, the smooth surface layer, the drug layer, the covering layer, the covering layer, the drug layer, the smooth surface layer, the smooth surface layer, the drug layer, and the covering layer formed on the PET film), with a circular blade having a diameter of 15 mm, so as not to reach the back surface of the PET film (see FIG. 7), or by a method of delaminating the PET film on the back surface from the laminated product of film form obtained as the intermediate product (d) to obtain the laminated edible layer only, and then punching out the laminated edible layer with a circular blade (see FIG. 6). Table 5 shows the ratio of ingredients.

TABLE 5

| Layer | Ingredient | Amount relative to the amount of solid gram of each layer [g] | Content in one piece of preparation [mg] |
|---|---|---|---|
| Covering layer | Pullulan | 84 | 23.52 |
| | Sucrose fatty acid ester | 1 | 0.28 |
| | Concentrated glycerine | 15 | 4.2 |
| | Subtotal | 100 | 28 |
| Drug layer | Mulberry leaf powder | 25 | 10 |
| | α-starch | 35 | 14 |
| | Enzyme denatured starch | 25 | 10 |
| | Trehalose | 5 | 8 |
| | Concentrated glycerine | 9.9 | 3.96 |
| | Sucralose | 0.1 | 0.04 |
| | Subtotal | 100 | 40 |
| Smooth surface edible layer | α-starch | 35 | 8.4 |
| | Enzyme denatured starch | 50 | 12 |
| | Trehalose | 5 | 1.2 |
| | Concentrated glycerine | 9.9 | 2.376 |
| | Sucralose | 0.1 | 0.024 |
| | Subtotal | 100 | 24 |

Comparative Example 3

An attempt was made to prepare a mulberry leaf containing sustained release food sheet by a producing method described below without forming a smooth surface edible layer.

<Preparation of Covering Layer Solution>

To an appropriate amount of water, 15.0 parts by weight of concentrated glycerine was added and stirred. In addition, to a small amount of ethanol, 1.0 parts by weight of sucrose fatty acid ester was added and dissolved while stirring, and the resulting solution was added to the foregoing glycerine aqueous solution. To the resulting solution, 84.0 parts by weight of pullulan was added and dissolved while stirring to obtain a covering layer solution.

<Preparation of Irregular Surface Edible Layer (Drug Layer) Solution>

To an appropriate amount of water, 5.0 parts by weight of trehalose was added and dissolved while stirring. Then, to the resulting solution, 9.9 parts by weight of concentrated glycerine was added and stirred. In addition, 15.0 parts by weight of mulberry leaf powder (average particle size 20 to 30 μm, particle size distribution 99 μm all pass), 35.0 parts by weight of α-starch, 30.0 parts by weight of enzyme denatured starch, and 0.1 parts by weight of sucralose was sufficiently mixed. The sufficiently mixed powder was added to the foregoing aqueous solution, and mixed while stirring to obtain a drug layer solution.

<Irregular Surface Edible Layer Forming Step>

On the unwinding shaft 51 of the coating apparatus 50 in FIG. 9, a PET film whose back surface was subjected to silicone release treatment was set, and the covering layer solution was supplied to the dam portion 57 to coat the covering layer solution on a front surface (a surface that is not subjected to the silicone release treatment) of the PET film, and then dried at a drying temperature of 80° to form an edible covering layer of 32 μm thick.

The PET film provided with the covering layer was again set to the unwinding shaft 51, and the drug layer solution was coated on the covering layer, and dried at a drying temperature of 80° to form a drug layer of 80 μm thick having an irregular surface (112 μm in two layers) (intermediate product (a)). The irregularities in the intermediate product (a) were measured by a digital thickness gauge SMD-565 (produced by TECLOCK) to recognize that a height difference of the irregularities was 20 μm at the highest.

<Pressure Bonding and Resin Film Delaminating Step>

The intermediate products (a) wound in the rolls were set to the upper unwinding shaft 13 and the lower unwinding shaft 14 of the pressure bonding apparatus 10 in FIG. 1. The edible layers having irregular surfaces of the unwound intermediate product (a) were introduced into the nip between the pair of press rolls 15, 15 so that they face each other, and bonded together at a pressure bonding temperature of 40° C. and a pressure of 1.0 MPa and laminated.

An attempt was made to draw the PET film only located on an upper surface of the bonded edible layers that reach 30° C. by natural heat dissipation after passing through the press rolls 15, 15 along the peripheral surface of the film delamination roll 17, wind up the PET film on the delaminated film winding shaft 18 to be delaminated from the bonded edible layers, and then wind up the PET film retaining the bonded edible layers on the winding shaft 19 into a roll. However, the bonded edible layers were separated into their original states on the delamination roll 17, the covering layer and the drug layer before pressure bonding were still retained on the resin film 16a wound up on the delaminated film winding shaft 18, and the covering layer and the drug layer before pressure bonding were also still retained on the resin film 16b wound upon the winding shaft 19, and thus the layers cannot be pressure bonded.

Table 6 shows the ratio of ingredients of the preparation.

TABLE 6

| Layer | Ingredient | Amount relative to the amount of solid gram of each layer [g] | Content in one piece of preparation [mg] |
| --- | --- | --- | --- |
| Covering layer | Pullulan | 84 | 23.52 |
| | Sucrose fatty acid ester | 1 | 0.28 |
| | Concentrated glycerine | 15 | 4.2 |
| | Subtotal | 100 | 28 |
| Drug layer | Mulberry leaf powder | 15 | 10.5 |
| | α-starch | 35 | 24.5 |
| | Enzyme denatured starch | 30 | 21 |
| | Trehalose | 5 | 3.5 |
| | Concentrated glycerine | 9.9 | 6.93 |
| | Sucralose | 0.1 | 0.07 |
| | Subtotal | 100 | 70 |

INDUSTRIAL APPLICABILITY

According to the method for producing an orally administrable edible agent of aggregated substance-containing laminate film form using the pressure bonding technique in which the edible layers having the irregular surfaces due to the presence of the aggregated substance are pressure bonded with the edible layer substantially free of any aggregated substance interposed therebetween, and an orally administrable edible agent obtained by the method according to the present invention, the orally administrable edible agent of laminate film form can be obtained having the multilayer structure including laminated extremely thin layers with high productivity that allows edible layers having irregular surfaces due to the presence of aggregated substance to be reliably pressure bonded, can improve quantitative accuracy required for pharmaceutical preparations, and prevents time constraint in a drying step or the like, as compared with the conventional lamination coating technique of repeating coating and drying of the coating liquid to form the multilayer structure.

Further, in the laminated structure obtained by the conventional lamination coating technique, the boundary between the laminated edible layers appears unclear and blurred, and the ingredients of the edible layers permeate and mix in the boundary. On the other hand, in the laminated structure obtained by the method of the present invention using the pressure bonding technique, the boundary between the edible layers can be definitely identified, and the ingredients of the edible layers do not permeate and mix. This prevents drug decomposition or unintended reactions caused by mixing of part of the ingredients of the edible layers to improve preservation stability, and allows accurate control of the concentration of the active ingredient in each edible layer.

The invention claimed is:

1. A method for producing an orally administrable edible agent of aggregated substance-containing laminate film form, said method comprising, pressure bonding edible layers, each having an irregular surface due to the presence of an aggregated substance, wherein the pressure bonding occurs with the irregular surfaces of the edible layers facing each other, and an edible layer substantially free of any aggregated substance interposed between the edible layers having the irregular surfaces, wherein an irregular surface is a surface having uneven distribution of granular or powdery aggregated substance.

2. A method for producing an orally administrable edible agent of aggregated substance-containing laminate film form, said method comprising:

(A) an irregular surface edible layer forming step for forming an irregular surface edible layer having an irregular surface with a predetermined thickness by directly or indirectly coating a coating liquid containing an aggregated substance on a resin film;

(B) a smooth surface edible layer forming step for forming an edible layer having a substantially smooth surface with a predetermined thickness on a resin film by coating;

(C) a pressure bonding step for joining together the edible layers formed on the resin films obtained in said irregular surface edible layer forming step (A) and said smooth surface edible layer forming step (B) so that the edible layers face each other, and pressurizing the resin films at back surfaces to bond the edible layers together;

(D) a resin film delaminating step for delaminating only the resin film used in said smooth surface edible layer forming step (B) among the resin films on both sides of the bonded edible layers obtained in said pressure bonding step (C);

(E) a multiple edible layer pressure bonding step for joining together the bonded edible layers having a substantially smooth surface formed on the resin film obtained in said resin film delaminating step (D) and an irregular surface edible layer made of the same or different ingredient as or from said irregular surface edible layer and provided with has an irregular surface due to the presence of aggregated substance formed on the resin film in said irregular surface edible layer forming step (A) so that the edible layers face each other, and pressurizing the resin films at back surfaces to bond said edible layers together; and (F) a resin film separating step for delaminating at least one of the resin films on both sides of the bonded edible layers obtained in said multiple edible layer pressure bonding step (E), wherein a smooth surface is a surface substantially free of granular or powdery aggregated substance, and an irregular surface is a surface having uneven distribution of granular or powdery aggregated substance.

3. A method for producing an orally administrable edible agent of aggregated substance-containing laminate film form, said method comprising:

(A) an irregular surface edible layer forming step for forming an irregular surface edible layer having an irregular surface with a predetermined thickness by directly or indirectly coating a coating liquid containing an aggregated substance on a resin film;

(B) a smooth surface edible layer forming step for forming an edible layer having a substantially smooth surface with a predetermined thickness on a resin film by coating;

(C) a pressure bonding step for joining together the edible layers formed on the resin films obtained in said irregular surface edible layer forming step (A) and said smooth surface edible layer forming step (B) so that the edible layers face each other, and pressurizing the resin films at back surfaces to bond the edible layers together;

(D) a resin film delaminating step for delaminating only the resin film used in said smooth surface edible layer forming step (B) among the resin films on both sides of the bonded edible layers obtained in said pressure bonding step (C);

(G) a multiple bonded edible layers pressure bonding step for joining together the bonded edible layers having a substantially smooth surface formed on the resin film obtained in said resin film delaminating step (D) and bonded edible layers made of the same or different ingredient as or from said bonded edible layers and provided with a substantially smooth surface formed on the resin film through said irregular surface edible layer forming step (A), said smooth surface edible layer forming step (B), said pressure bonding step (C), and said resin film delaminating step (D) so that the edible layers face each other, and pressurizing the resin films at back surfaces to bond the edible layers together; and (H) a resin film separating and removing step for delaminating at least one of the resin films on both sides of the bonded edible layers obtained in said multiple bonded edible layers pressure bonding step (G), wherein a smooth surface is a surface substantially free of granular or powdery aggregated substance, and an irregular surface is a surface having uneven distribution of granular or powdery aggregated substance.

4. A method for producing an orally administrable edible agent of aggregated substance-containing laminate film form, said method comprising:

(A) an irregular surface edible layer forming step for forming an irregular surface edible layer having an irregular surface with a predetermined thickness by directly or indirectly coating a coating liquid containing an aggregated substance on a resin film;

(I) a coating smooth surface edible layer forming step for forming an edible layer having a substantially smooth surface with a predetermined thickness by coating on the irregular surface of the edible layer formed on the resin film obtained in said irregular surface edible layer forming step (A);

(J) a coating edible layer pressure bonding step for joining together a coating laminated edible layer having a substantially smooth surface formed on the resin film obtained in said coating smooth surface edible layer forming step (I), and an irregular surface edible layer made of the same or different ingredient as or from said irregular surface edible layer and provided with an irregular surface due to the presence of aggregated substance formed on the resin film in said irregular surface edible layer forming step (A) so that the edible layers face each other, and pressurizing the resin films at back surfaces to bond said edible layers together; and (K) a resin film delaminating step for delaminating at least one of the resin films on both sides of the bonded edible layers obtained in said coating edible layer pressure bonding step (J), wherein a smooth surface is a surface substantially free of granular or powdery aggregated substance, and an irregular surface is a surface having uneven distribution of granular or powdery aggregated substance.

5. A method for producing an orally administrable edible agent of aggregated substance-containing laminate film form, said method comprising:

(A) an irregular surface edible layer forming step for forming an irregular surface edible layer having an irregular surface with a predetermined thickness by directly or indirectly coating a coating liquid containing an aggregated substance on a resin film;

(I) a coating smooth surface edible layer forming step for forming an edible layer having a substantially smooth surface with a predetermined thickness by coating on the irregular surface of the edible layer formed on the resin film obtained in said irregular surface edible layer forming step (A);

(L) a multiple coating laminated edible layer pressure bonding step for joining together a coating laminated edible layer having a substantially smooth surface formed on the resin film obtained in said coating smooth surface edible layer forming step (I), and a coating laminated edible layer made of the same or different ingredient as or from said coating laminated edible layer and provided with a substantially smooth surface formed on the resin film through said irregular surface edible layer forming step (A) and said coating smooth surface edible layer forming step (I) so that the edible layers face each other, and pressurizing the resin films at back surfaces to bond the edible layers together; and (M) a resin film delaminating and removing step for delaminating at least one of the resin films on both sides of the bonded edible layers joined in said multiple coating laminated edible layer pressure bonding step (L), wherein a smooth surface is a surface substantially free of granular or powdery aggregated substance, and an irregular surface is a surface having uneven distribution of granular or powdery aggregated substance.

6. A method for producing an orally administrable edible agent of aggregated substance-containing laminate film form, said method comprising:

(A) an irregular surface edible layer forming step for forming an irregular surface edible layer having an irregular surface with a predetermined thickness by directly or indirectly coating a coating liquid containing an aggregated substance on a resin film;

(B) a smooth surface edible layer forming step for forming an edible layer having a substantially smooth surface with a predetermined thickness on a resin film by coating;

(C) a pressure bonding step for joining together the edible layers formed on the resin films obtained in said irregular surface edible layer forming step (A) and said smooth surface edible layer forming step (B) so that the edible layers face each other, and pressurizing the resin films at back surfaces to bond the edible layers together;

(D) a resin film delaminating step for delaminating only the resin film used in said smooth surface edible layer forming step (B) among the resin films on both sides of the bonded edible layers obtained in said pressure bonding step (C);

(N) a multiple coating bonded edible layers pressure bonding step for joining together bonded edible layers having a substantially smooth surface formed on the resin film obtained in said resin film delaminating step (D) and a coating laminated edible layer made of the same or different ingredient as or from said bonded edible layer and provided with an edible layer having a substantially smooth surface with a predetermined thickness formed by coating on the irregular surface of the edible layer formed on the resin film in said irregular surface edible layer forming step (A) so that the edible layers face each other, and pressurizing the resin films at back surfaces to bond the edible layers together; and (O) a resin film removing step for delaminating at least one of the resin films on both sides of the bonded edible layers joined in said multiple coating bonded edible layers pressure bonding step (N), wherein a smooth surface is a surface substantially free of granular or powdery aggregated substance, and an irregular surface is a surface having uneven distribution of granular or powdery aggregated substance.

7. The method for producing an orally administrable edible agent of aggregated substance-containing laminate film form according to any one of claims 1 to 6, wherein a pressure when said edible layers are joined and pressure bonded is 0.05 to 1.5 Mpa, and a temperature of the edible layers at that time is 30° C. to 70° C.

8. The method for producing an orally administrable edible agent of aggregated substance-containing laminate film form according to claim 7, wherein after said edible layers are pressure bonded and before the resin film is delaminated from said bonded edible layers, said bonded edible layers are cooled to a temperature 10° C. or more lower than the temperature of the edible layers in the pressure bonding, and the temperature of the cooled edible layers is kept higher than 0° C.

9. The method for producing an orally administrable edible agent of aggregated substance-containing laminate film form according to any one of claims 1 to 6, wherein a thickness of the edible layer containing an aggregated substance and having an irregular surface is 25 to 300 um.

10. The method for producing an orally administrable edible agent of aggregated substance-containing laminate film form according to any one of claims 1 to 6, wherein said aggregated substance is an active ingredient having a physiological activity.

11. The method for producing an orally administrable edible agent of aggregated substance-containing laminate film form according to any one of claims 1 to 6, wherein each of said edible layers to be bonded together contains an edible thermoplastic substance.

12. The method for producing an orally administrable edible agent of aggregated substance-containing laminate film form according to claim 11, wherein said edible thermoplastic substance includes at least one selected from the group consisting of amylose, carboxymethyl cellulose potassium, carboxymethyl cellulose sodium, carboxymethyl cellulose calcium, alkyl ester alginate, ethyl cellulose, eudragit, carboxymethylethylcellulose, carboxymethyl starch, carboxymethyl cellulose, agar, gelatin, shellac, dextran, dextrin, starch, tragacanth, hydroxyethylcellulose, hydroxypropylcellulose, hydroxypropylmethylcellulose, polyvinylpyrrolidone, methacrylic acid copolymer, and methylcellulose phthalate.

13. The method for producing an orally administrable edible agent of aggregated substance-containing laminate film form according to any one of claims 1 to 6, wherein each of said edible layers to be bonded together contains an edible non-thermoplastic substance and an edible thermoplastic substance.

* * * * *